United States Patent
Parvizi et al.

(10) Patent No.: US 11,471,088 B1
(45) Date of Patent: Oct. 18, 2022

(54) HANDHELD OR WEARABLE DEVICE FOR RECORDING OR SONIFYING BRAIN SIGNALS

(71) Applicants: The Board of Trustees of the Leland Stanford Junior University, Redwood City, CA (US); Ceribell, Inc., Sunnyvale, CA (US)

(72) Inventors: Josef Parvizi, Palo Alto, CA (US); Christopher D. Chafe, Woodside, CA (US); Xingjuan Chao, Palo Alto, CA (US); Ronald C. Eddington, Jr., Los Gatos, CA (US)

(73) Assignees: The Board of Trustees of the Leland Stanford Junior University, Stanford, CA (US); Ceribell, Mountain View, CA (US)

( * ) Notice: Subject to any disclaimer, the term of this patent is extended or adjusted under 35 U.S.C. 154(b) by 0 days.

(21) Appl. No.: 15/159,759

(22) Filed: May 19, 2016

Related U.S. Application Data

(60) Provisional application No. 62/163,637, filed on May 19, 2015.

(51) Int. Cl.
*A61B 5/04* (2006.01)
*A61B 5/0478* (2006.01)
(Continued)

(52) U.S. Cl.
CPC .............. *A61B 5/316* (2021.01); *A61B 5/291* (2021.01); *A61B 5/4094* (2013.01); *A61B 2562/0219* (2013.01)

(58) Field of Classification Search
CPC . A61B 5/04017; A61B 5/0478; A61B 5/4094; A61B 2562/0219; A61B 5/316; A61B 5/291
See application file for complete search history.

(56) References Cited

U.S. PATENT DOCUMENTS 3,837,331 A * 9/1974 Ross .................... A61B 5/0476
128/905
3,927,663 A * 12/1975 Russell ................ A61B 5/0456
128/901
(Continued)

FOREIGN PATENT DOCUMENTS

EP 2113194 A1 11/2009
WO WO 2004000115 A1 * 12/2003 ........... A61B 5/0478
(Continued)

OTHER PUBLICATIONS

Dombois et al, The Sonification Handbook (Chapters 12-15), 2011, Logos Verlag: Berlin, Germany, pp. 301-397.*
(Continued)

*Primary Examiner* — Andrey Shostak
(74) *Attorney, Agent, or Firm* — Lumen Patent Firm

(57) ABSTRACT

A handheld device for sonifying electrical signals obtained from a subject is provided. The device can utilize at least one of several operations including (but not limited) digitizing signals from electrodes, adjusting the signals based on accelerometer input, filtering the signals, conditioning the signals according to conditioning parameters, modulating the signal according to sound synthesis parameters, and generating sound from the representations of the signals to accomplish sonification. The device can include an analog-to-digital (A/D) converter to digitize the one or more electrical signals and a processor that receives the one or more digitized electrical signals and produces a representation of an acoustic signal. The device further includes a speaker system that sonifies the representation of the acoustic signal.

21 Claims, 18 Drawing Sheets

(51) Int. Cl.
*A61B 5/00* (2006.01)
*A61B 5/316* (2021.01)
*A61B 5/291* (2021.01)

(56) References Cited

U.S. PATENT DOCUMENTS

| | | | |
|---|---|---|---|
| 4,018,121 A | 4/1977 | Chowning et al. | |
| 4,883,067 A | 11/1989 | Knispel et al. | |
| 5,730,140 A * | 3/1998 | Fitch | A61B 5/0205 600/514 |
| 5,995,868 A * | 11/1999 | Dorfmeister | A61B 5/048 600/300 |
| 7,555,344 B2 | 6/2009 | Maschino et al. | |
| 7,881,778 B2 | 2/2011 | Rantala | |
| 8,620,643 B1 | 12/2013 | Ludwig et al. | |
| 8,644,915 B2 | 2/2014 | Chou | |
| 8,855,775 B2 | 10/2014 | Leyde | |
| 8,885,464 B2 | 11/2014 | Micu et al. | |
| 8,927,847 B2 | 1/2015 | Chafe et al. | |
| 2007/0067003 A1 | 3/2007 | Sanchez et al. | |
| 2007/0218084 A1 | 9/2007 | Caleo et al. | |
| 2008/0228100 A1* | 9/2008 | Navakatikyan | A61B 5/0476 600/544 |
| 2009/0082831 A1* | 3/2009 | Paul | A61N 1/0456 607/59 |
| 2009/0292180 A1 | 11/2009 | Mirow | |
| 2011/0308376 A1* | 12/2011 | Ludwig | G10H 1/06 84/604 |
| 2012/0197092 A1 | 8/2012 | Luo et al. | |
| 2013/0245422 A1* | 9/2013 | D'arcy | A61B 5/0484 600/409 |
| 2013/0324878 A1* | 12/2013 | Chafe | A61B 5/7415 600/544 |
| 2015/0093729 A1 | 4/2015 | Plans et al. | |
| 2015/0150520 A1 | 6/2015 | Chafe et al. | |

FOREIGN PATENT DOCUMENTS

| | | | |
|---|---|---|---|
| WO | 2007123923 | A2 | 11/2007 |
| WO | 2009133484 | A1 | 11/2009 |
| WO | 2010129026 | A2 | 11/2010 |
| WO | 2014006596 | A1 | 1/2014 |
| WO | 2016005403 | A1 | 1/2016 |

OTHER PUBLICATIONS

Freitas, The DC Blocking Filter, 2007, Web, Retrieved from: https://www.mathworks.com/matlabcentral/fileexchange/13792thedcblockingfilter.*

Haas et al, Strategies for Adapting Automated Seizure Detection Algorithms, 2007, Med Eng Phys, 29(8): 895-909.*

Valjamae et al, A Review of Real-Time EEG Sonification Research, 2013, International Conference on Auditory Display, Poland, 85-93.*

Winters et al (1/F Noise and Auditory Aesthetics: Sonification of a Driven Bead Pile, 2011, The 17th International Conference on Auditory Display, pp. 1-5).*

Lu et al (Scale-Free Brain-Wave Music from Simultaneously EEG and fMRI Recordings, 2012, PLoS One, 7(11): e49773, doi:10.1371/journal.pone.0049773).*

Sriraam (A High-Performance Lossless Compression Scheme for EEG Signals Using Wavelet Transform and Neural Network Predictors, 2012, International Journal of Telemedicine and Applications, vol. 2012, Article ID 302581, 8 pages, doi:10.1155/2012/302581).*

Lee (Data Sonification Using Formant synthesis, 2004, Web, Retrieved from: http://www-ccrma.stanford.edu:80/~kglee/sonification/formant_synthesis/formant_synthesis.html).*

Plessey Semiconductors Ltd., Application Note #291566, Non-contact ECG measurement using EPIC, Mar. 22, 2012, 5 pgs.

"ECG sensor in a SmartPhone", Plessey Semiconductors Ltd., Application Note #291474, ECG sensor in a SmartPhone, Dec. 2, 2011, 2 pgs.

"Epic . . . ECG at your fingertips", Plessey Semiconductors Ltd., Epic . . . ECG at your fingertips, Overview, EPIC Healthcare—Plessey Semiconductors, printed on Nov. 21, 2013 from http://www.plesseysemiconductors.com/epic-healthcare-plessey-semiconductors.php, 4 pgs.

"Epic . . . ECG at your fingertips", Plessey Semiconductors Ltd., Epic . . . ECG at your fingertips, Technical Information, EPIC Healthcare—Plessey Semiconductors, printed on Nov. 21, 2013 from www.plesseysemiconductors.com/epic-healthcare-plessey-semiconductors.php, 6 pgs.

"Holter monitor", From Wikipedia, the free encyclopedia, printed on Feb. 17, 2016 from https://en.wikipedia.org/wiki/Holter_monitor, 5 pgs.

"NeuroSky: Body and Mind. Quantified.", printed on Jan. 14, 2015 from http://neurosky.com/, 10 pgs.

"Polar Wearlink®+ Transmitter with Bluetooth®", Polar USA, printed on Nov. 21, 2013 from https://www.polar.com/us-en/products/accessories/Polar_WearLink_transmitter_with_Blu, 2 pgs.

"What is an Electrocardiogram (EKG or ECG) Test?", WebMD, Heart Disease Health Center, Electrocardiogram, printed on Nov. 21, 2013 from http://www.webmd.com/heart-disease/electrocardiogram, 5 pgs.

De Campo et al., "New Sonification Tools for EEG Data Screening and Monitoring", Proceedings of the 13th International Conference on Auditory Display, Montreal, Canada, 536-542 (2007).

Dubus et al., "A Systematic Review of Mapping Strategies for the Sonification of Physical Quantities", PLoS One 8(12), 32 pgs. (2013).

Elgendi et al., "Real-Time Wireless Sonification of Brain Signals", Advances in Cognitive Neurodynamics (III), 175-181 (2013).

Grond et al., "Aesthetic strategies in sonification", AI & Society 27(2), 213-222, doi:10.1007/s00146-011-0341-7 (2012).

Hermann et al., "Kernel Regression Mapping for Vocal EEG Sonification", Proceedings of the 14th International Conference on Auditory Display, Paris, France, Jun. 24-27, 2008, 7 pgs.

Hermann et al., "Vocal Sonification of Pathologic EEG Features", Proceedings of the 12th International Conference on Auditory Display, London, UK, Jun. 20-23, 2006, 6 pgs.

Hinterberger et al., "Auditory Feedback of Human EEG for Direct Brain-Computer Communication", Proceedings of ICAD 04—Tenth Meeting of the International Conference on Auditory Display, Sydney, Australia, Jul. 6-9, 2004, 5 pgs.

Hinterberger et al., "POSER: Parametric Orchestral Sonification of EEG in Real-Time for the Self-Regulation of Brain States", Proceedings of the International Workshop on Interactive Sonification, Bielefeld University, Germany, Jan. 8, 2004, 6 pgs.

Jovanov et al., "Perceptualization of Biomedical Data: An Experimental Environment for Visualization and Sonification of Brain Electrical Activity", IEEE Engineering in Medicine and Biology Magazine 18(1), 50-55 (1999).

Mealla et al., "Sonification of Brain and Body Signals in Collaborative Tasks Using a Tabletop Musical Interface", The 17th International Conference on Auditory Display, Budapest, Hungary, 5 pgs. (2011).

Vialatte et al., "Sparse Bump Sonification: a New Tool for Multi-channel EEG Diagnosis of Brain Disorders", Riken Brain Science Institute, Tech. Rep., 18 pgs. (2009).

Vickers, Paul "Sonification for Process Monitoring", The Sonification Handbook, Chapter 18, Hermann, T., Hunt, A., Neuhoff, J. G., editors, Logos Publishing House, Berlin, Germany, 455-491 (2011).

Baier et al., "Event-based sonificaton of EEG rhythms in real time", Clinical Neurophysiology, 2007; 118(6): 1377-1386, Epub Mar. 29, 2007, 10 pgs.

Baier et al., "Sonified Epileptic Rhythms", Proceedings of the 12th International Conference on Auditory Display, London, UK, Jun. 20-23, 2006.

Vialatte et al, "Sparse Bump Sonification: A New Tool for Multi-channel EEG Diagnosis of Mental Disorders; Application to the Detection of the Early of Alzheimer's Disease", ICONIP 2006, Part III, LNCS 4234, pp. 92-101, 2006, 10 pgs.

(56) References Cited

OTHER PUBLICATIONS

Weiner et al., "The Sound of One Arm Swinging: A Model for Multidimensional Auditory Display of Physical Motion", Proceedings of the 12th International Conference on Auditory Display, London, UK, Jun. 20-23, 2006.

Baier G, Hermann T, Stephani U. Event-based sonification of EEG rhythms in real time. Clin Neurophysiol. 2007;118(6):1377-86.

Hinterberger T. The Sensorium: A Multimodal Neurofeedback Environment. Advances in Human-Computer Interaction. 2011;2011:1-10.

Vialatte. Sparse Bump Sonification: a New Tool for Multichannel EEG Diagnosis of Mental Disorders; Application to the Detection of the Early Stage of Alzheimer's Disease. In: King et al. Neural Information Processing Lecture Notes in Computer Science. ICONIP 2006. , vol. 4234: Springer, Berlin, Heidelberg; 2014.

Loui P, Koplin-Green M, Frick M, Massone M. Rapidly learned identification of epileptic seizures from sonified EEG. Front Hum Neurosci. 2014;8:820.

Hermann T, Baier G, Stephani U, Ritter H, editors. Vocal Sonification of Pathologic EEG Featur. Proceedings of the 12th International Conference on Auditory Display; 2006; London.

DeCampo A, Hoeldrich R, Eckel G, Wallisch A, editors. New Sonification Tools for EEG Data Screening and Monitoring. Proceedings of the 13th International Conference on Auditory Display; 2007; Montreal, Canada.

Hermann T, Baier G, Stephani U, Ritter H, editors. Kernel Regression Mapping for Vocal EEG Sonification. Proceedings of the 14th International Conference on Auditory Display; 2008; Paris—France.

Steffert T, Väljamäe A, editors. Prototyping a Method for the Assessment of Real-Time EEG Sonifications. The 21st International Conference on Auditory Display (ICAD); 2015; Graz, Austria.

Dombois F, Eckel G, Audification. The Sonification Handbook; Hermann, Hunt, Neuhof, Eds. 2011; Logos;pp. 301-324.

* cited by examiner

HANDHELD OR WEARABLE DEVICE FOR RECORDING OR SONIFYING BRAIN SIGNALS

CROSS-REFERENCE TO RELATED APPLICATIONS

The present application claims priority under 35 U.S.C. § 119(e) to U.S. Provisional Patent Application Ser. No. 62/163,637 entitled "Handheld or Wearable Device for Recording or Sonifying Brain Signals" filed May 19, 6015. The disclosure of U.S. Provisional Patent Application Ser. No. 62/163,637 is hereby incorporated by reference in its entirety.

TECHNICAL FIELD

The disclosed embodiments relate generally to the field of sonifying signals detected from a living subject (e.g., electrical signals indicative of brain activity and/or heart activity), and in particular, to a handheld or wearable device for sonifying signals from a living subject.

BACKGROUND

The ability to measure signals from a living subject (e.g., relating to the living subject's bodily functions) is beneficial for medical and diagnostic applications. For example, from a diagnostic point of view, measuring brain signals helps to ascertain brain activity related to abnormal brain function, to monitor spatial and/or temporal progression of brain disease, to aid surgical or nonsurgical intervention by localizing disease-sites in the brain, and to monitor brain activity of a healthy subject or a subject of unknown health status when the subject experiences a variety of stimuli and lack of stimuli.

However, the use of electrical signals received from, for example, the brain (e.g., electroencephalography (EEG) signals) often requires a great deal of resources. Conventional EEG tests are typically performed at specialized centers (e.g., tertiary care centers), by specialized technicians, and the results are interpreted by specialized doctors (e.g., neurologists). Thus, conventional EEG is not typically available to, e.g., first responders in an acute emergency. Instead, the first responders must rely on external signs (e.g., level of consciousness or shaking) when deciding whether a patient may have a neurological problem. Because conventional EEG is beyond the resources of even some hospitals, a patient with suspected neurological problems will often be taken to a specialized center. Even at a specialized center, it may take hours to obtain EEG results and have the results interpreted by a neurologist.

Every year in the United States alone, about 10 million people are seen in emergency departments (ED) for evaluation of altered mental state (AMS). Additionally, 5 million patients with critical conditions are admitted to intensive care units (ICU). Some of these are admitted through EDs but a majority of the patients are either transferred directly from other hospitals or are cases with postsurgical complications. In these patients, electroencephalography (EEG) is the gold-standard test for detecting seizures. While there are many causes of AMS, seizures are one of the most frequently suspected. About 10-20% of ICU patients are subject to seizures, and 90% of seizures in ICUs are non-convulsive. Where EEG is available, physicians order it to rule in/out ongoing non-convulse status epilepticus (NOSE). If the diagnosis of NOSE is made quickly, it will precipitate appropriate acute management, and will reduce unnecessary diagnostic procedures, length of hospitalization, and morbidity.

In the US alone, about 20,000 patients die of NOSE. These patients have other severe co-morbidities but ongoing non-convulsive seizures will be a significant contributing factor to their extremely high mortality rate. In fact, NOSE has a mortality rate higher than the mortality rate of convulsive status epilepticus partly because of lack of obvious behavioral signs of seizures (e.g., convulsions), which delays detection and treatment. EEG is the only way to detect ongoing seizures. Early diagnosis of NOSE is life-saving for these patients and every hour of delay in diagnosis counts. Mortality of patients with NOSE treated with a delay of 20 hours is twice as high as those treated within 30 minutes.

Because EEG is one of the oldest diagnostic tools in neurology, and because it has shown promise in saving lives, one would assume that it is widely integrated into medical practice everywhere and one might think that it is equally available to all populations at risk. This is unfortunately not the case. Inequality of access exists even in the United States, and at a wider scale on the global stage. Many hospitals in the US cannot offer an EEG platform. In addition to purchasing expensive EEG platforms, a given hospital has to hire certified EEG techs and neurologists with training in clinical electrophysiology and maintain an on-call schedule leading to a substantial management cost. For hospitals without a large number of neurological cases, this is simply not a wise investment. If they have patients with AMS in whom they suspect seizures, the patient is transferred to a larger tertiary hospital. As a result, a large number of patients may be held in NOSE condition before they are transferred.

In hospitals with EEG capability, acquiring an EEG may take hours. There may also be a longer delay from the time the EEG is acquired to the time the ordering physician receives the diagnostic information. If the EEG tech is not on duty in the hospital premises, it may take even longer. There is also a significant financial waste in using the EEG platform where it is available (especially in the United States). Many more EEGs are ordered and acquired than the number of seizures detected by these EEGs. In a retrospective review of 300 EEGs, only 1% of EEGs acquired in the ED had ongoing seizures, yet more than 95% of EEGs were ordered to confirm or rule out seizures.

The current EEG practice in the outpatient ambulatory setting also suffers from significant limitations. Patients with paroxysmal events (e.g., transient confusional state or loss of awareness) are referred to 12-48 hours of EEG monitoring at home. The recording may yield useful information only if it captures one of the infrequent paroxysmal events. Moreover, patients with dementia cannot even be tested with continuous EEG for a long period of time given their inability to follow instructions. Patients with dementia have increased risk of subclinical seizures which may in part contribute to worsening of their memory loss. About 3 million people in the United States suffer from unprovoked seizures whose occurrence is unpredictable. When patients with seizure do not recover fully, there is always a concern that they may be having indolent subclinical seizures. Parents of infants and children with such seizures take them for evaluation in local hospitals. By the time they reach the hospital, seizures may have stopped.

Traditional approaches to measuring signals from a living subject (e.g., location-specific brain signals, or electrocardiography (ECG) signals corresponding to heart activity)

typically involve recording and visually displaying electrical signals acquired from the brain or other organs. Moreover, these approaches are typically used for diagnostic or scientific purposes. When represented in visual or graphical form, subtle features and attributes—and subtle changes in features and attributes—of the electrical signals may not be easily discernible. However, when sonified or converted to auditory form, these subtle features and attributes can become more apparent. Furthermore, sonification methodologies that transform the signals acquired from the living subject into vocal patterns and vocal parameters—and changes in vocal patterns and vocal parameters—that resemble a human voice make it easier to discern, upon auditory inspection, subtleties in the underlying electrical signals that correspond to bodily functions.

Additionally, traditional approaches to measuring signals from a living subject have not focused on applications beyond diagnostics and scientific research. To that end, a method of sonifying signals obtained from a living subject is provided. In particular, in some embodiments, the method transforms signals acquired from the living subject into vocal patterns and vocal parameters that can be used for applications in entertainment as well as medical diagnostics and research.

Therefore, there is a need for devices and methods that increase the availability of the diagnostic benefits of analyzing electrical signals received from a living subject's brain. In addition, traditional methods of measuring and analyzing signals from a living subject have not focused on sonification (e.g., aural presentation) of the signals.

SUMMARY OF THE INVENTION

Systems and methods for sonification of electroencephalogram signals using sonification devices in accordance with embodiments of the invention are disclosed herein. In one embodiment, a device for sonifying signals includes an input port configured to receive at least one electroencephalogram signal produced by a plurality of electrodes, the electroencephalogram signals are indicative of brain activity, an analog-to-digital converter to digitize the at least one electroencephalogram signal; an accelerometer to indicate mechanical movement affecting the at least one electroencephalogram signal; a filter, where the filer is configured to filter non-seizure-related brain wave features from the at least one digitized signal; a processor that receives the at least one digitized signals and is directed by machine readable instructions to produce a sonification of the at least one electroencephalogram signal by performing a set of operations in real time. The set of operations include conditioning the at least one digitized signals according to conditioning parameters, and modulating the at least one digitized signals according to sound synthesis parameters to produce an audio signal. The device for sonifying signals further includes a speaker system configured to generate sound based upon an audio signal output by the processor. The processor of the device interrupts sonification of the at least one electroencephalogram signal when the accelerometer indicates mechanical movement affecting the at least one electroencephalogram signal above a particular threshold. The processor of the device resumes sonification of the at least one electroencephalogram signal when the accelerometer indicates mechanical movement affecting the at least one electroencephalogram signal has returned below the particular threshold.

In a further embodiment, the filter filters the at least one digitized signal utilizing filter bandpass cutoffs as part a dual-stage filter. In another embodiment, at least one of DC-bias, AC line contamination, and non-seizure-related brain wave features are rejected by the filter bandpass cutoffs. In a still further embodiment, the dual-stage filter comprises a first stage with a first-order pole-zero infinite impulse response DC-blocking filter and a second stage with a finite impulse response filter.

In still another embodiment, conditioning the at least one digitized signal brings the at least one digitized signals into range for sonification and enhances contrasts within the at least one digitized signal. In a yet further embodiment, modulating the at least one digitized signals according to sound synthesis parameters further includes continuously modulating vocal sound parameters according to sound synthesis parameters including at least one of pitch, loudness and vowel quality. In a further embodiment again, the processor sonifies the representation of the at least one electroencephalogram signal using at least one lookup table that consolidates formant pitch mapping and inverse pitch frequency mapping.

In another embodiment again, a device for sonifying signals includes an input port configured to receive at least one electroencephalogram signal produced by a plurality of electrodes, where the electroencephalogram signals are indicative of brain activity, an analog-to-digital converter to digitize the at least one electroencephalogram signal, an accelerometer to indicate mechanical movement affecting the at least one electroencephalogram signal, a filter, where the filer is configured to filter non-seizure-related brain wave features from the at least one digitized signal, a processor that receives the at least one digitized signals and is directed by machine readable instructions to produce a sonification of the at least one electroencephalogram signal by performing a set of operations in real time. The set of operations includes conditioning the at least one digitized signal by bringing the at least one digitized signal into a predetermined range for sonification and enhancing contrast between components within the at least one digitized signal, and modulating the at least one digitized signal by continuously modulating vocal sound parameters according to sound synthesis parameters including at least one of pitch, loudness and vowel quality to produce an audio signal. The device includes a speaker system configured to generate sound based upon an audio signal output by the processor. The processor interrupts sonification of the at least one electroencephalogram signal when the accelerometer indicates mechanical movement affecting the at least one electroencephalogram signal above a particular threshold. The processor resumes sonification of the at least one electroencephalogram signal when the accelerometer indicates mechanical movement affecting the at least one electroencephalogram signal has returned below the particular threshold.

In another embodiment again, a method for sonifying signals using a sonification device is provided, the method includes receiving at least one electroencephalogram signal produced by a plurality of electrodes using an input port of a sonification device, where the electroencephalogram signals are indicative of brain activity, digitizing the at least one electroencephalogram signal using an analog-to-digital converter of the sonification device, receiving an indication of mechanical movement affecting the at least one electroencephalogram signal using an accelerometer of the sonification device, filtering non-seizure-related brain wave features from the at least one digitized signal using a filter of the sonification device, producing a sonification of the at least one electroencephalogram signal by performing a set of operations in real time using a processor of the sonification device. The set of operations includes conditioning the at least one digitized signals according to conditioning parameters, and modulating the at least one digitized signals according to sound synthesis parameters to produce an audio signal. The method further includes generating sound based upon an audio signal output using a speaker system of the sonification device, interrupting sonification of the at least one electroencephalogram signal when the accelerometer indicates mechanical movement affecting the at least one electroencephalogram signal above a particular threshold, and resuming sonification of the at least one electroencephalogram signal when the accelerometer indicates mechanical movement affecting the at least one electroencephalogram signal has returned below the particular threshold.

In another additional embodiment, the filter of the sonification device filters the at least one digitized signal utilizing filter bandpass cutoffs as part a dual-stage filter. In a still yet further embodiment, at least one of DC-bias, AC line contamination, and non-seizure-related brain wave features are rejected by the filter bandpass cutoffs. In still yet another embodiment, the dual-stage filter comprises a first stage with a first-order pole-zero infinite impulse response DC-blocking filter and a second stage with a finite impulse response filter.

In a still further embodiment again, conditioning the at least one digitized signal brings the at least one digitized signals into range for sonification and enhances contrasts within the at least one digitized signal. In still another embodiment again, modulating the at least one digitized signals according to sound synthesis parameters further comprises continuously modulating vocal sound parameters according to sound synthesis parameters including at least one of pitch, loudness and vowel quality. In a still further additional embodiment, the processor sonifies the representation of the at least one electroencephalogram signal using at least one lookup table that consolidates formant pitch mapping and inverse pitch frequency mapping.

BRIEF DESCRIPTION OF THE DRAWINGS

Like reference numerals refer to corresponding parts throughout the drawings.

DETAILED DESCRIPTION

Figure 1A:
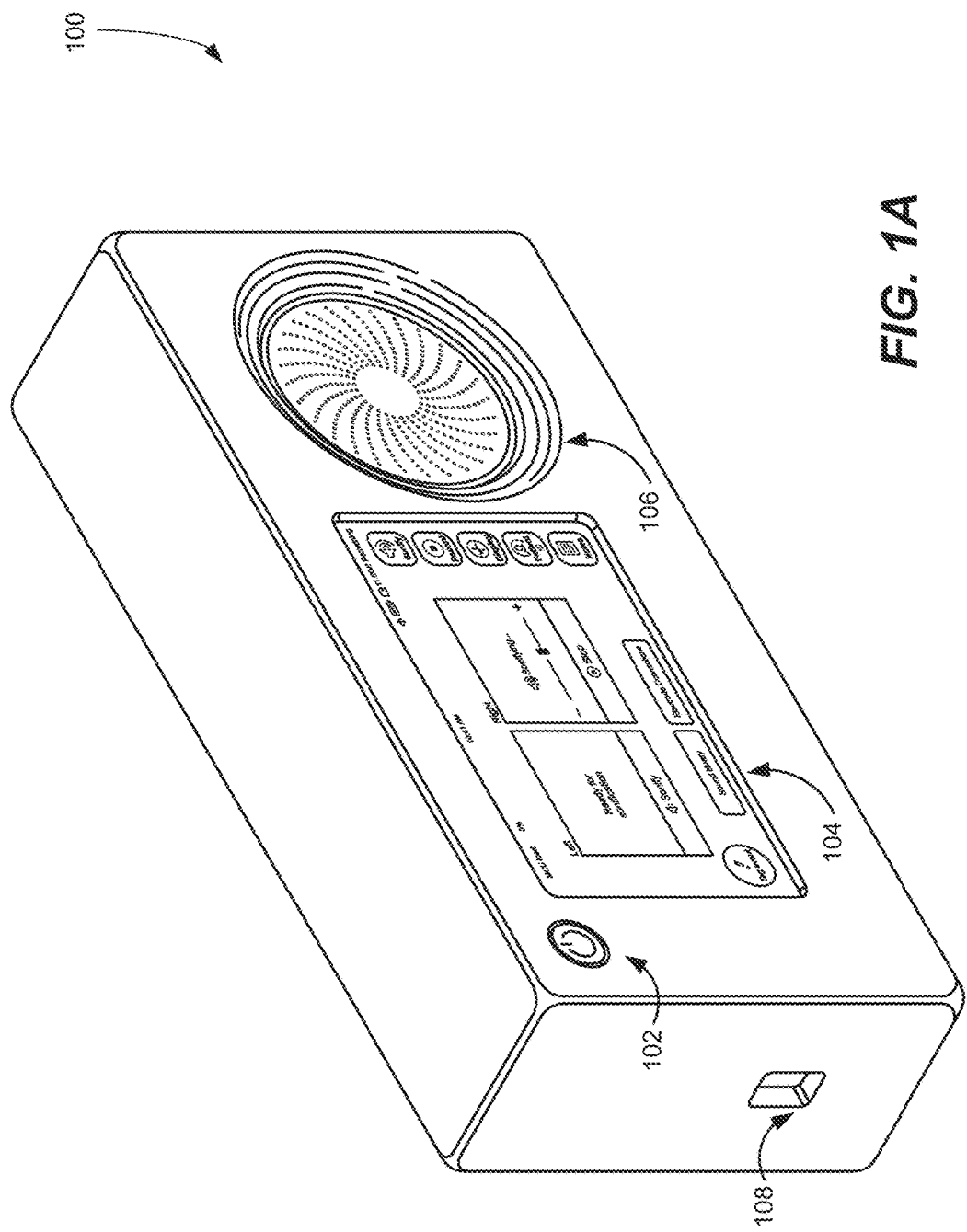
FIGS. 1A-1B are illustrations of a handheld device for sonifying electrical signals obtained from a subject, in accordance with some embodiments of the invention.

Turning now to the drawings, handheld sonification devices that sonifiy signals (e.g., EEG signals received from electrodes on a living subject) in real time to audio signals for instant diagnostic evaluation in accordance with various embodiments of the invention are illustrated. The sonified signals help listeners differentiate seizures from non-seizures. Previous experimentation has shown greater than 85% to 97% accuracy by even lay individuals in differentiating seizures from non-seizures when utilizing sonification devices in accordance with some embodiments of the invention.

The sonification devices can include embedded software and/or hardware instructions that direct the sonification devices to perform a number of operations during sonification. Sonification devices in accordance with many embodiments utilize a unique combination of three core operations to produce human comprehendible sound that indicates the presence or lack thereof of seizure symptoms from electrical signals. The produced sounds have human recognizable vowel and tonal sound. These three core operations can include signal conditioning, parameter modulation, and sound generation. Moreover, a multitude of embodiments of particular importance expand upon these three core operations and can optionally further include new schemes for digitization of the signal, adjustments to the signal based on accelerometer input, and further techniques for filtration of the signal.

Signal conditioning can be an initial stage in some embodiments, which acquires raw sensor data before analyzing it. During signal conditioning, many embodiments process incoming real-time signals (e.g., EEG signals gathered from electrodes placed on a living subject) to bring the signals into range for sonification and enhancing contrasts. Signal conditioning can also include filtering out less important frequencies and DC-bias (i.e., the mean value of the waveform of the signal). In a number of embodiments, a combination of different filters, compressor processes, and upsampling processes are utilized as appropriate to the requirements of different sonification applications. Moreover, sonification devices in accordance with many embodiments of the invention utilize particular coefficient tunings for filtering, scaling and thresholds determined through exhaustive testing to measure changes in ranges of these values against the specificity and sensitivity of listeners ability to distinguish seizure from non-seizure states.

Parameter modulation uses the conditioned signal to continuously modulate vocal sound parameters according to matrices of sound synthesis parameters such as (but not limited to) pitch, loudness and vowel (timbral) quality. Parameter modulation can further include audification. Audification usually is thought to refer to time-base manipulation such as speeding up or slowing down playback rate so that inaudible low-frequency or high-frequency signals are shifted into our range of hearing. With this technique a wide range of time series data becomes audible (from slow seismic to ultra-fast physics). Previous audification methods rely on time-base shifting (e.g., by compressing the EEG signals ~60 times) whereas various embodiments of the invention can utilize direct listening to low-frequency without distorting the temporal information.

By comparison to audification, "sonification" typically refers to translation of data to sound through manipulation of parameters in some sound-producing instrument. For example, a piano can be played by quarterly gross domestic product (GDP) values. Translation of these values into a sequence of piano notes can be accomplished by mapping the GDP range to a desired range of pitches. In several embodiments, the range of the EEG signal is mapped to a pitch range but without distorting the EEG signal by directly applying it as a pitch modulation. Some embodiment further map the same signal to loudness and vowel parameters, in parallel.

In a number of embodiments, the sound generation process produces audible sound via vocal synthesizers. The produced sound can be computer-generated sung vowels in real time. This end result is a continuous sound that can provide a listener with exactly what is needed to distinguish seizure and seizure-like states from non-seizure states. In certain embodiments, the sonification device is capable of executing these operations in real time on a handheld device to perform EEG-to-sound sonification.

As noted above, sonification devices in accordance with many embodiments of the invention can be handheld or wearable devices that sonify electrical signals obtained from a subject (e.g., a living subject such as a human or a non-human animal). In some embodiments, the device includes a plurality of electrodes configured to be placed at respective locations inside the brain during neurosurgical procedures. The plurality of electrodes produces one or more electrical signals corresponding to brain activity. In several embodiments, the device includes an input port configured to couple a plurality of electrodes to the device and to receive the one or more electrical signals produced by the plurality of electrodes. In certain embodiments, the plurality of electrodes includes a first electrode (or a first set of electrodes) that is configured to be placed at any of a plurality of locations on the subject's head. That is to say, the first electrode (or first set of electrodes) is capable of being moved (e.g., intended to be moved) to different locations on the subject's head (e.g., as described with reference to FIGS. 9A-9C and FIGS. 10A-10B). The device further includes an analog-to-digital (A/D) converter to digitize the one or more electrical signals, a processor that receives the one or more digitized electrical signals and produces a digital representation of an acoustic signal, and a speaker system that converts the digital representation of the acoustic signal to an output sound (and/or an output port through which to pass the produced acoustic signal to an external speaker (and/or an output port through which to pass the produced representation of the acoustic signal to an external speaker).

In a number of embodiments, the device is intended for use by patients, patients' family members, emergency medical personnel and/or medical doctors who are not neurologists (e.g., emergency room physicians). As can readily be appreciated, however, the device can also be a vital tool for neurologists. In some embodiments, the device includes memory (and/or makes use of cloud-based memory external to the device) that stores the EEG data. The stored EEG data allows a specialist (e.g., a neurologist) to review the EEG data (and/or sonified data) after an acute episode has passed. For example, consider a patient who visits a neurologist complaining of occasional episodes of altered mental status (AMS). In a conventional medical test for AMS, a neurologist will send the patient home with adhesive electrodes (e.g., ten or more electrodes) applied to her head along with a device to record the data from the electrodes. This type of test is sub-optimal for a number of reasons. First, it is unpleasant for the patient to have the adhesive electrodes applied to their head, resulting in a maximum of twenty-four to forty-eight hours during which the electrodes can stay on the patient. Second, if the patient's episodes only occur on average once a month, there's a high probability that the portable EEG device will not capture an episode and the inconvenience will be for naught.

In accordance with some embodiments, the electrodes of the devices described herein are applied adhesively or non-adhesively (e.g., with wet or dry electrodes) by the patient when an episode begins, thus addressing both problems. Furthermore, in some circumstances, the patient is instructed to place the handheld device at a plurality of positions on her head. For example, the patient may be instructed by the neurologist to, upon noticing the onset of an episode, place the handheld device's electrodes on the left side of her head for a short period of time (seconds to minutes) seconds and then place the handheld device's electrodes on the right side of her head for the same amount of time. Alternatively, if the patient suffers from a condition that renders them unconscious, unresponsive, and/or unreliable during such episodes, a friend or family member can be instructed to do the same.

Consider, as another example, use of the handheld device by emergency medical personnel (e.g., emergency department physicians and/or field medical personnel such as emergency medical technicians). When a patient that is unconscious, unresponsive, and/or unreliable (more generally known as having an altered mental status) arrives in the emergency department or is discovered in the field, in some circumstances, the emergency medical personnel will apply the electrodes of the devices described herein to one or more locations on the patient's head (e.g., both sides of the patient's head). The sonified electrical signals obtained from various locations on the patient's head will manifest differently depending on the patient's brain condition. For example, bilateral silence and/or quiet are, in some embodiments, representative of brain death. Sonified electrical signals that are quieter on one side of the patient's head than the other in some circumstances represent a stroke. Rhythmic activity in the sonified electrical signals in some circumstances represents a seizure. Thus, the sonified electrical signals produced by the devices described herein, in accordance with some embodiments, provide early clues to medical providers that may help direct the patient to an appropriate medical center (e.g., a stroke center) and/or obviate the need for expensive, time-consuming, and potentially risky medical procedures (e.g., lumbar punctures, colloquially known as spinal taps). The devices described herein also provide an inexpensive option to medical facilities that do not have access to EEG capabilities.

In addition, sonification devices in accordance with various embodiments of the invention can be useful for assessing neurological and/or other conditions in non-human animals. Thus, a veterinarian may, in some circumstances, use the devices described herein to "auscultate" (e.g., by sonifying, as described below) brain signals from non-human animals.

Reference will now be made in detail to various embodiments, examples of which are illustrated in the accompanying drawings. In the following detailed description, numerous specific details are set forth in order to provide a thorough understanding of the invention and the described embodiments. However, the invention is optionally practiced without these specific details. In other instances, well-known methods, procedures, components, and circuits have not been described in detail so as not to unnecessarily obscure aspects of the embodiments.

For ease of explanation, various embodiments are described below with reference to sonification of signals representing brain activity (e.g., electroencephalography (EEG) signals) of a living subject. However, one of skill in the art will recognize that signals representing other bodily functions (e.g., electrocardiography (ECG) signal, an electromyography (EMG) signal, or an electronystagmography (ENG) signal, a pulse oximetry signal, a capnography signal, a photoplethysmography signal), and/or any other detectable signal may be substituted, or used in addition to (e.g., in conjunction with), one or more signals representing brain activity.

A. Sonification Devices

Figure 1B:
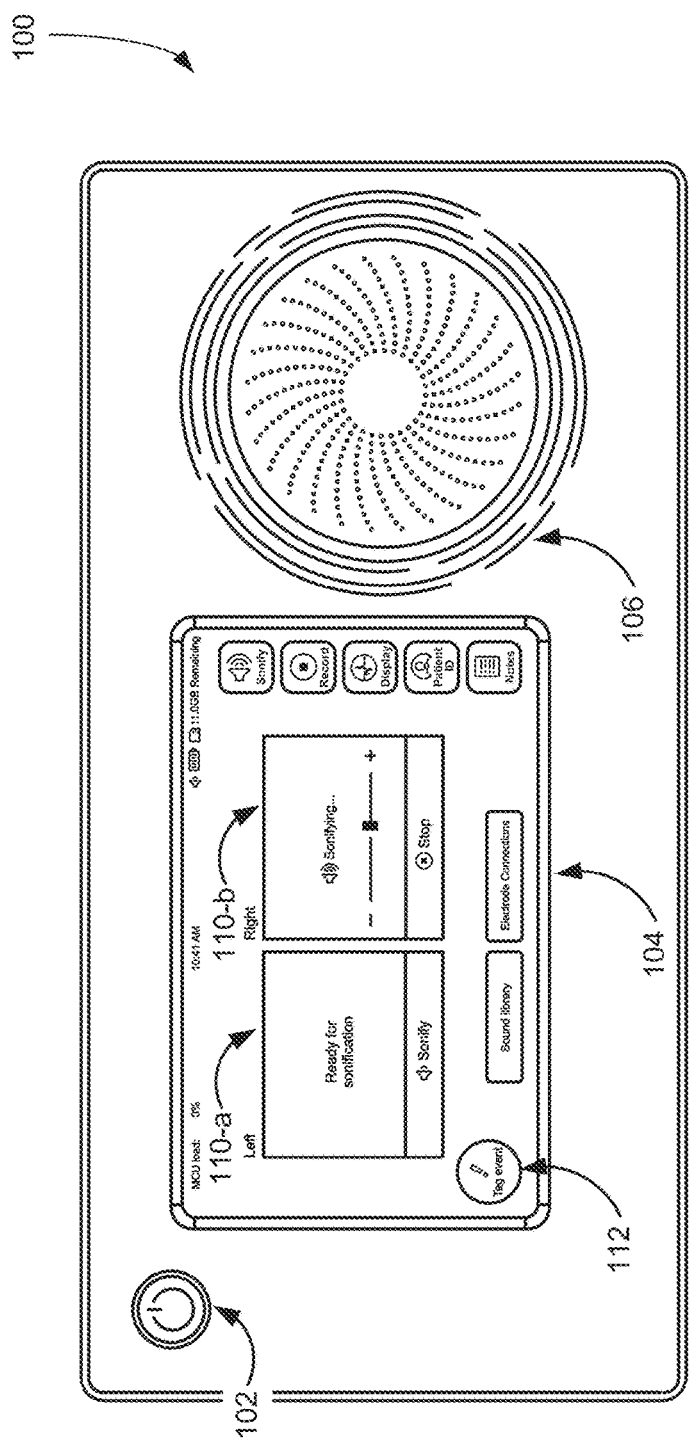
Figure 2:
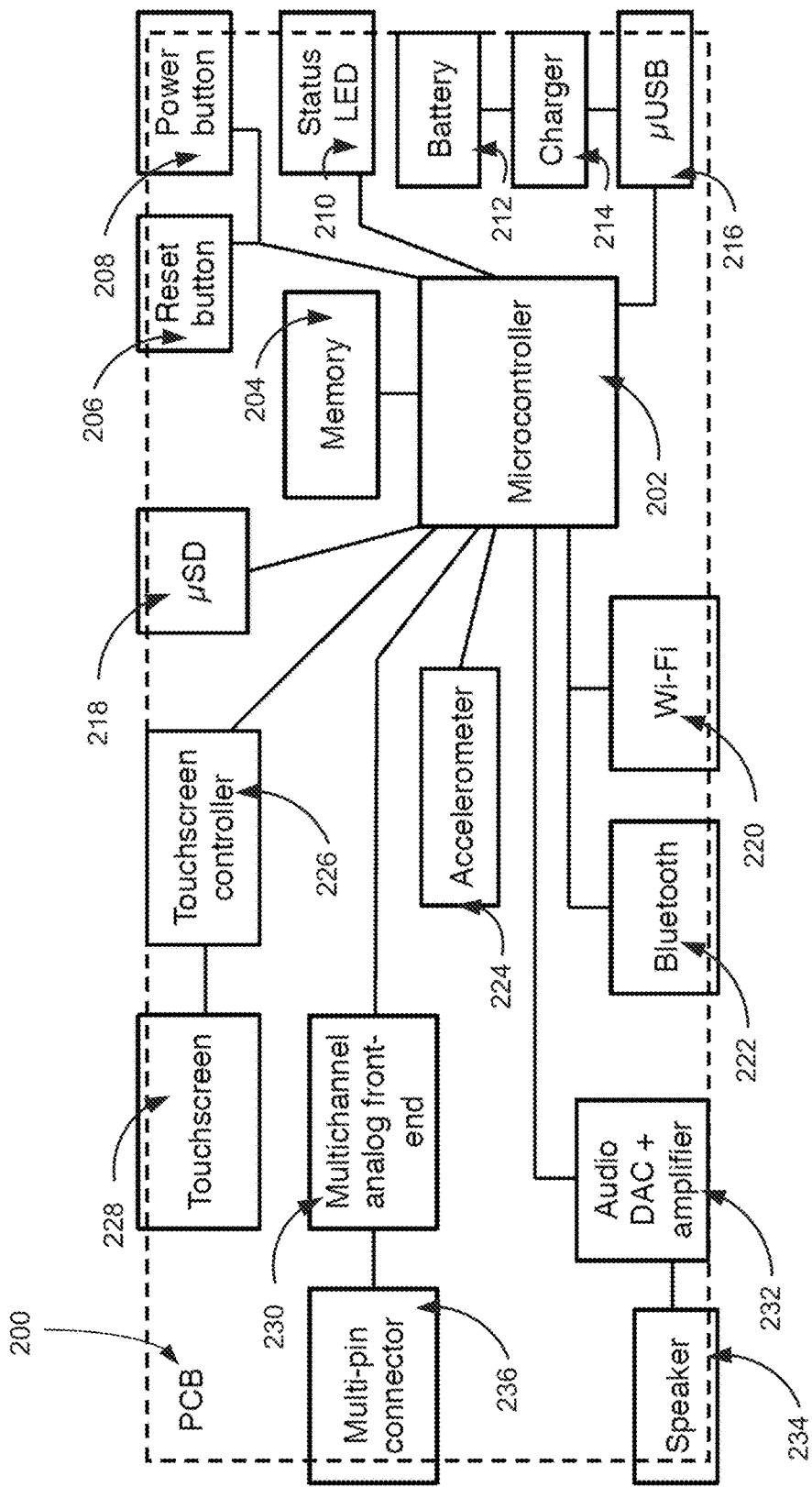
FIG. 2 is a circuit diagram for a sonification device, in accordance with some embodiments of the invention.

FIGS. 1A-1B are illustrations of a handheld sonification device 100 for sonifying electrical signals obtained from a subject, in accordance with some embodiments of the invention. Sonification device 100 can receive signals from signal capturing devices. Several signal capturing devices are described below in accordance with embodiments of the invention; specifically, device 900 (FIGS. 9A-90), device 1000 (FIGS. 10A-10B), and/or device 1100 (FIG. 11). In various embodiments, device 100 may share any of the features described below with reference to device 900 (FIGS. 9A-9C), device 1000 (FIGS. 10A-10B), and/or device 1100 (FIG. 11), unless context makes clear that such features are incompatible with device 100. Likewise, device 900, device 1000, and/or device 1100 may share any of the features described with reference to sonification device 100 unless context makes clear that such features are incompatible with a respective one of those signal capturing devices.

Sonification device 100 can include an input port 808 configured to couple to a plurality of electrodes (not shown) to sonification device 100 and to receive electrical signals produced by the plurality of electrodes. The electrical signals correspond to the subject's brain activity. Sonification device 100 can include an analog-to-digital (A/D) converter (e.g., analog-to-digital converter 608, FIG. 6C) to digitize the electrical signals. Sonification device 100 can further include one or more processors that receive the digitized electrical signals and produce a representation of an acoustic signal based on the digitized signals (e.g., in accordance with process 800, FIGS. 8A-8C and/or process 300, FIG. 3). The sonification device can include a speaker system 806 that sonifies the representation of the acoustic signal.

Sonification device 100 can be a "pocket sized" device. Sonification device 100 can include a power button 802 and a display 804 (e.g., an LCD display/touch screen). The electrodes can be tethered to the sonification device 100 through input port 808. Sonification device 100 can received electrical signals via the input port 808. The received electrical signals can correspond to a subject's brain activity, received through input port 808. The brain activity can include a first electrical signal corresponding to left-hemisphere brain activity and a second electrical signal corresponding to right-hemisphere brain activity. The output acoustic signal can include independently audible voices corresponding to each of the first electrical signal and the second electrical signal.

Display 804 can display a graphical user interface that can enable a user of the sonification device 100 to independently control the two voices (acoustic signals or acoustic signal portions) corresponding to the distinct sensors, one for each hemisphere of the subject's brain, and their time-domain signals. For example, display 804 includes display region 810-a corresponding to the left-hemisphere signal and display region 810-b corresponding to the right hemisphere signal. In some embodiments, display regions 810 include affordances (e.g., buttons, touch screen buttons) for controlling sonification of the respective signals (e.g., turning on/off the sonification of the respective signals and/or controlling other properties of the respective sonified signals). In the example shown in FIGS. 1A-1B, the user is sonifying the right-hemisphere signal (e.g., display region 810-b says "Sonifying"), but not the left-hemisphere signal (e.g., display region 810-a says "Ready for sonification"). The graphical user interface also includes other display regions/affordances for navigating the graphical user interface. For example, the graphical user interface can display EEG signals graphically, set parameters for recording EEG signals, input information about the patient, write notes, etc. The graphical user interface also can include a button to tag events, e.g., so that a non-specialist can tag a particular time in a recording of a sonified signal, which can be reviewed by a specialist later.

FIG. 200 conceptually illustrates a circuit board 200 of a sonification device in accordance with some embodiments. The example circuit board 200 includes a microcontroller 202, a memory 204, a reset button 206, a power button 208, a status LED 210, a battery 212, a charger 214, a micro-USB interface 216, a micro-SD card reader 218, a Wi-Fi interface 220, a Bluetooth interface 222, an accelerometer 224, touchscreen controller 226, a touchscreen 228, a multichannel analog front-end 230, an audio Digital-to-Analog Converter (DAC) and amplifier 232, a speaker 234, and a multi-pin connector 236. Different embodiments can include different combinations and/or sub-combinations components than those shown in the example circuit board 200 in FIG. 200. Real-time deadlines for digital sound generation are exacting. If the firmware misses a deadline, annoying clicks (brief sound dropouts) can be heard. Circuit 200 was architected to support consistent audio on a relatively inexpensive processor. The relatively inexpensive processor suggested the use of a firmware interrupt scheme for performing sonification operations. As can readily be appreciated, modifications to the circuitry can be contemplated as more powerful processors and/or real time operating systems are utilized in the implementation of the sonification device. The sonification operations of some embodiments are discussed in detail below.

B. Processes for Sonifying Signals

Figure 3:
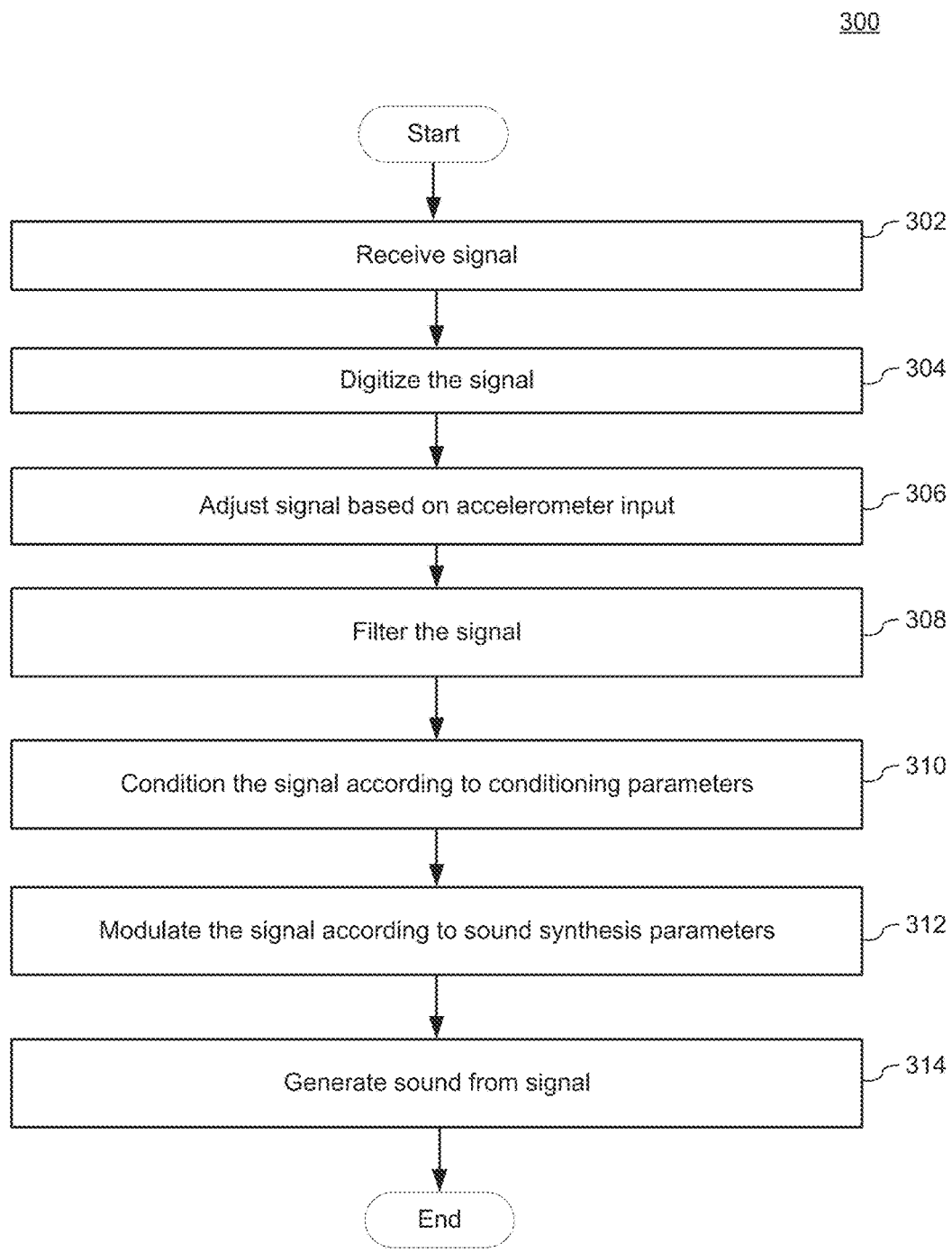
FIG. 3 is a flow chart illustrating a process for sonifying signals capable of being performed by a sonification device in accordance with some embodiments of the invention.

FIG. 3 is a flowchart illustrating a process 300 for sonifying signals according to an embodiment of the invention. Process 300 can be applied in sonifying electrical activity (e.g., electrical signals) obtained from a subject. Process 300 can be performed by a handheld and/or wearable sonification device in accordance with multiple embodiments of the invention; such as device 900 of FIGS. 9A-9C, device 1000 of FIGS. 10A-10B, device 1100 of FIG. 11, and/or device 100 of FIGS. 1A-1B). Process 300 is optionally governed by instructions that are stored in a computer readable storage medium and that are executed by a digital processor system (or, optionally, one or more digital processor systems) (e.g., digital processor system 560, which in various embodiments is or is a component of any of the aforementioned handheld or wearable devices). The operations shown in FIG. 3 optionally correspond to instructions stored in a computer memory or computer readable storage medium. The computer readable storage medium optionally includes a magnetic or optical disk storage device, solid state storage devices such as flash memory, or other non-volatile memory device or devices. The computer readable instructions stored on the computer readable storage medium are in source code, assembly language code, object code, or another instruction format that is interpreted by one or more processors. Various embodiments of the invention can implement portions and/or all of process 300 in sonifying signals. Moreover, the operations process 300 can be implemented as sub-processes or in connection with other processes described herein as in accordance with embodiments of the invention.

Process 300 can include receiving (302) one or more signals. The received signals can be electrical signals produced by a plurality of electrodes and received via input ports to a handheld sonification device. The one or more electrical signals can correspond to a subject's brain activity. In some embodiments, the device includes a plurality of electrodes, while in several other embodiments the device includes an input port that is coupled to the plurality of electrodes (e.g., the electrodes are tethered to the device). In certain embodiments, a plurality of representations of acoustic signals is combined to produce a combined acoustic signal. Alternatively, a combined acoustic signal can be generated by combining acoustic signals corresponding to the plurality of representations of acoustic signals produced by the digital processor system. In yet another alternative, a plurality of acoustic signals, each corresponding to one or more of the aforementioned representations of acoustic signals, are recorded on distinct tracks, where the distinct tracks are configured to enable concurrent playback of the acoustic signals recorded in those tracks.

Process 300 can include digitizing (304) the received signal. The digitization can be accomplished on one or more electrical signals using an analog-to-digital converter. An analog-to-digital converter converts a continuous analog input signal (e.g., acoustic signals) to a digital number that represents the quantity's amplitude. Most embodiments of the invention, when implemented as a sonification device, include hardware analog-to-digital converters of sufficient quality and/or number of quantization levels to minimize errors introduced by the digitization. In several embodiments, the digitization process involves oversampling which refers to a process that samples at a rate that is significantly higher than the Nyquist frequency (i.e. twice the highest frequency component) of a bandlimited digitized signal.

In order to mitigate against subject mechanical movement, process 300 can include adjusting (306) the signals based on accelerometer input. In some circumstances, the mechanical movement is due to a medical condition of the patient (e.g., a seizure and/or head shaking). In some embodiments, the mechanical movement is due to an environment in which the device is being used (e.g., the device is being used in the back of a moving ambulance). The mechanical movement can introduce artifacts that are in fact rhythmic and thus the listener may mistake the artifact rhythms for seizures.

In some embodiments, the devices performing process 300 can include an accelerometer that produces the one or more signals indicative of mechanical movement of a subject (e.g., the accelerometer is within the device's housing). In some embodiments, the sonification device performing process 300 includes an accelerometer interface for receiving the one or more signals indicative of mechanical movement of a subject. In some embodiments, the sonification device performing process 300 includes a second input port (e.g., coupled with the accelerometer interface) for receiving one or more signals indicative of mechanical movement of the subject (e.g., the accelerometer is external to the devices performing process 300 and is tethered to the devices performing process 300 through the second input port). In some embodiments, the accelerometer is located on the subject (e.g., attached to the subject or attached to an article of clothing worn by the subject).

Process 300 can then adjust (306) the one or more digitized signals based on the one or more signals indicative of mechanical movement. In some embodiments, adjusting the one or more digitized electrical signals based on the one or more signals indicative of mechanical movement includes: in accordance with a determination that an amplitude of the one or more signals indicative of mechanical movement is above a predefined movement threshold, forgoing sonification of the acoustic signal (e.g., the devices performing process 300 rejects the EEG signals by forgoing sonification). In order words, process 300 interrupts and pauses sonification of the signal due to detecting mechanical movement from an accelerometer. Conversely, in accordance with a determination that the amplitude of the one or more signals indicative of mechanical movement is below the predefined movement threshold, the process 300 sonifies the acoustic signal (e.g., process 300 accepts the EEG signal). In some embodiments, process 300 displays an indication of whether the EEG signal is being accepted or rejected (e.g., on a display or using a blinking LED).

Process 300 can include filtering (306) the one or more signals. In several embodiments, filtering the one or more signals includes configuring a first filter (e.g., a high-pass filter) in accordance with the one or more signals indicative of mechanical movement and applying the configured first filter to the one or more digitized electrical signals. In some embodiments, process 300 detects frequencies in mechanical movement and configures a frequency response of the first filter to attenuate the detected frequencies within the digitized electrical signals (e.g., the devices performing process 300 reshape the frequency response of the first filter, so that there is a change in the response of at least a first frequency with respect to the response of a second frequency). In many embodiments, configuring the first filter includes adjusting a cutoff frequency of the first filter. In various embodiments, configuring the first filter includes detecting prominent frequency modes in the mechanical movement and configuring the first filter to reject the prominent frequency modes in the digitized electrical signals (e.g., rejecting a fixed number of frequency modes, such as 3-5 modes, or rejecting any mode that has a power spectral density value in the mechanical movement above a predefined power threshold).

In several embodiments, filtering (308) the one or more signals includes, in accordance with one or more predefined criteria, applying a low-pass filter (e.g., a second filter) to the one or more digitized electrical signals. In yet further embodiments, the low-pass filter is intended to remove artifacts that are the results of convulsive muscle movements in the range of 70 Hz. In various embodiments, the low-pass filter has a cutoff frequency selected to remove artifacts that are the result of the convulsive muscle movements (e.g., a cutoff frequency below 70 Hz). In still yet more embodiments, the one or more predefined criteria are met when a user selects an option, via a user interface (e.g., the graphical user interface shown in FIGS. 1A-1B), to apply the low-pass filter. In other embodiments, the low-pass filter is applied in accordance with a determination that the subject is experiencing a seizure (e.g., the predefined criteria are seizure-detection criteria that are met when the process 300 determines that the subject is experiencing a seizure). In further additional embodiments, the devices performing process 300 are configured to detect a seizure using information garnered from the accelerometer signal (e.g., by analyzing the one or more signals indicative of mechanical movement of the subject). In further embodiments, the devices performing process 300 are configured to detect a seizure using the electrical signals corresponding to brain activity. In many embodiments, the devices performing process 300 use a combination of accelerometer information and brain activity information to detect a seizure. In additional embodiments, the low-pass filter is a digital low-pass filter. The digital low-pass filter can be implemented using software, firmware, hardware, or a combination thereof. In additional embodiments, the low-pass filter is an analog low-pass filter and the one or more signals are filtered before being digitized by the A/D converter.

In several embodiments, the filters employed by process 300 include EEG signal filter bandpass cutoffs. The EEG signal filter bandpass cutoffs can, according to some embodiments of the invention, be determined through testing. The EEG signal filter bandpass cutoffs can be utilized as part a dual-stage filter which is selective of only the signal features needed for recognition. DC-bias, AC line contamination, and non-seizure-related brain wave features can be rejected by employing EEG signal filter bandpass cutoffs. The first stage can be a first-order pole-zero Infinite impulse response (IIR) DC-blocker with a cutoff range of 0.1 Hz to 1.0 Hz. Experimentally, this configuration was found to be the optimal choice for rejecting analog front-end DC-bias. The second stage can be a 501-tap finite impulse response (FIR) filter with bandpass of 0.1-3.0 Hz to 5.0-15.0 Hz. An IIR equivalent can be less optimal because of resonance problems which created low-frequency ringing that was confused with signal features of interest. While particular embodiments and ranges and values were described herein with respect to specific filter values, reasonable variation on the values presented herein can be utilized as appropriate to the requirements of specific applications in accordance with various embodiments of the invention.

Process 300 can include conditioning (310) the signals according to conditioning parameters. Signal conditioning can be an initial stage in some embodiments, which acquires raw sensor data before analyzing it. During signal conditioning, many embodiments process incoming real-time signals (e.g., EEG signals gathered from electrodes placed on a living subject) to bring the signals into range for sonification and enhancing contrasts. Signal condition can include EEG rate processing according to particular signal conditioning parameters. EEG signal filter coefficients can be derived through offline testing on (actual, recorded) device signals and the best filter settings ported to the signal conditioning stage. Moreover, parameters specific to signal conditioning can be adapted according to various firmware configurations.

Other conditioning parameters of various other embodiments can include the following values as bases for ranges of success: thresholds of 1-25 µV, full-range scaling of 30-60 µV and compression of 1.5-3.0. Signal rectification i.e., absolute value can be applied to the filtered signal and then thresholding can be used to reject low-amplitude signal noise. Signal values below a threshold can be set to zero. Above a threshold signals can be scaled to create a fixed range of 0.0-1.0 with full range scaling and then can be compressed to raise the prominence of small features. Signal values can be boosted by taking the power-law exponent of the signal. In many instances, values which exceed full scale after compression can be clipped to full scale (1.0).

Process 300 can include modulating (312) the one or more signals according to sound synthesis parameters. Parameter modulation can include continuously modulating vocal sound parameters according to matrices of sound synthesis parameters such as pitch, loudness and vowel (timbral) quality. Parameter modulation refers to the matrix of sound synthesis parameters (pitch, loudness, vowel) and how a single conditioned EEG signal modulates each parameter in the group. Relationships can be expressed as offset and scale coefficients. The offset and scale coefficients can in many embodiments be determined ahead of device development in software-based research. The matrices determine the perceived identity of the vocal sound. While not necessarily a realistic replica of a singer, there is a recognizable "device identity" that can result from any particular matrix. The set of parameter coefficients chosen can make this identity invariant and almost trademark-like (for example, in the range of: "lll", "ahh", "ehh", "eee", "ohh", "ooo"). As an example, a sample matrix is provided herein will result in the following sonified output:

Pitch offset in the range of 50-150 Hz—This sets the "hum" base pitch of the vocalist for below-threshold EEG:
Pitch scale in the range of 110-440 Hz—This sets the pitch excursion for full-range EEG.
Amplitude offset in the range of 0.0001-0.01)—This sets the "hum" amplitude for below-threshold EEG.
Amplitude scale in the range of 0.05-2.0—This sets the maximum loudness for full-range EEG.
Vowel offset in the range of 0.0-1.0—This sets the "hum" vowel for below-threshold EEG.
Vowel scale in the range of 0.05-2.0—This sets the vowel interpolation amount for full-range EEG.
Vowel lookup table—a combination of these 6 vowels are used.

Process 300 can include generating (314) sound from the one or more signals. Device sound generation can be real-time and heard via onboard loudspeakers of devices performing process 300. The loudspeaker and device enclosure can affect sound quality. Most embodiments utilize particular speaker types and enclosure for better acoustics linearity.

For instance, a CUI Inc. MODEL: GF0401M can be utilized for good performance in several embodiments. This model provides for a speaker that is open to the front and to the inside of the enclosure. A different model, 1 cm smaller diameter, was 12 dB quieter and had a more nasal sound (the bottom octave of sound compared to the best choice was mostly missing). Enclosures which have been prototyped and tested included fully open, sandwich with open edges, and ported boxes. Ported boxes have been found to yield the best sound for most embodiments, the best sound being loud and resonant for rendering the vocalist "identity" as described above. As can readily be appreciated, the specific speaker and enclosure utilized in a sonification device largely depend upon the requirements of a given application.

Device sound generation is real-time and heard via an onboard loudspeaker. The loudspeaker and device enclosure affects sound quality. Real-time deadlines for digital sound generation are exacting. If the firmware misses a deadline, annoying clicks (brief sound dropouts) can be heard. Firmware in preferred embodiments was architected to support consistent audio on the relatively inexpensive processor chosen. Sound generation can take advantage of numerous hardware design techniques to speed up and enhance performance in numerous embodiments. The following discussion describes some of these techniques.

Sonification often requires mapping of data with a linear range into pitch frequencies of the human voice. The most common and natural way to do this is with the well-defined midi-to-frequency function: 440*2^(midinote-69)/12 which requires both a power and a divide operation. Sonification process 300 creates formant audio that avoids fringing effects, discontinuity clicks, phase distortion, spectral modulation, and other problems with simpler algorithms. However, the operations of process 300 utilize a division to calculate each formant harmonic as shown in the midi-to-frequency function. Thus a two formant synthesis with interpolation of between upper and lower frequencies involve 4 division operations (typically multiple clock cycle processor operations) per sample. Process 400 can eliminate these division operations using an interpolated look-up table for the inverse of the pitch frequency (look up of 1/f0), thus requiring only a multiply for each formant. Process 400 can be executed in conjunction with process 300 or as a subprocess of process 300.

Formant synthesis refers to creating audio signals that sound like a human singing voice or in more general terms, signals that have an acoustic resonance like the human vocal tract. Formant synthesis is useful in sonification applications where complex non-audio data is mapped to a human-like singing voice that can clarify or distinguish features in the data that may otherwise be difficult to detect. Process 400 provides for a fast method of synthesizing formant audio signals is described that achieves high quality real-time performance with a smaller, more efficient implementation in real-time embedded CPU/DSP processor firmware, FPGA, or ASIC devices. Process 400 receives (402) a signal for formant synthesis. This receipt can in many embodiments be in CPU/DSP processor firmware, FPGA, or ASIC devices.

Process 400 can include interpolating (404) signals using consolidated lookup tables. This consolidates interpolation for look-up into two tables for the formant pitch mapping and inverse pitch frequency mapping. The consolidation eliminates computationally expensive divide and power operations while maintaining synchronous operation and the interpolation of the pitch and formant frequencies from linear data.

Process 400 can include performing formant synthesis (406). High quality formant synthesis can in many embodiments be performed using a bank of linked oscillators, such as the phase-synchronous oscillators, where a single phasor is shared by the modulator and all carriers. In a typical implementation the bank is constructed with any number of harmonic outputs that are tapped off of a single common phasor. In practice, a bank of four (or more) carrier oscillators of this kind will can be used to generate a vocal sound. These can create human voice phonemes of 2 (or more) formants represented by a time-varying distribution pitch, harmonic, and amplitude. Process 400 can then complete sonification by generating (408) sound comparably to process 300 as discussed above.

Figure 4:
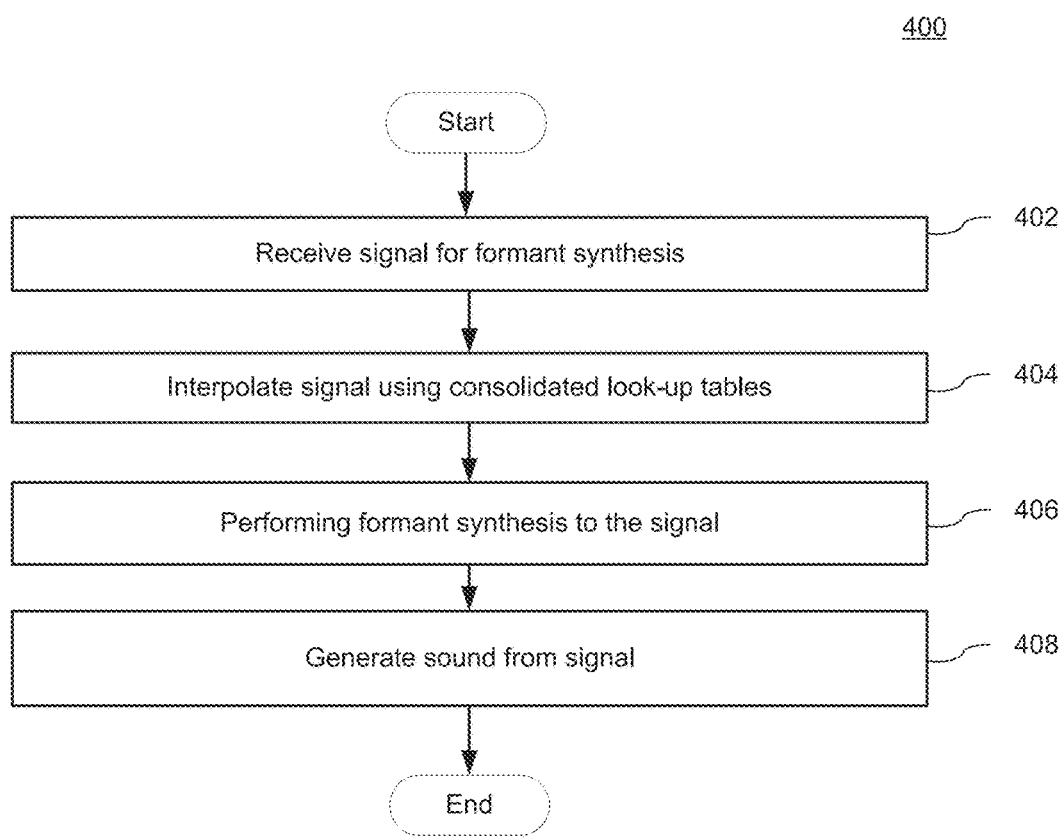
FIG. 4 is a flow chart illustrating a process for sonifying signals that takes advantage of certain hardware optimizations in accordance with some embodiments of the invention.

Although specific processes for sonification of EEG signals are described above with reference to FIGS. 3 and 4, any of a variety of signal processing and sonification processes can be utilized as appropriate to the requirements of a given application in accordance with various embodiments of the invention. Sonification devices and the interfacing of sonification devices in accordance with a number of embodiments of the invention are discussed further below.

C. Exemplary Body Interface System

Figure 5:
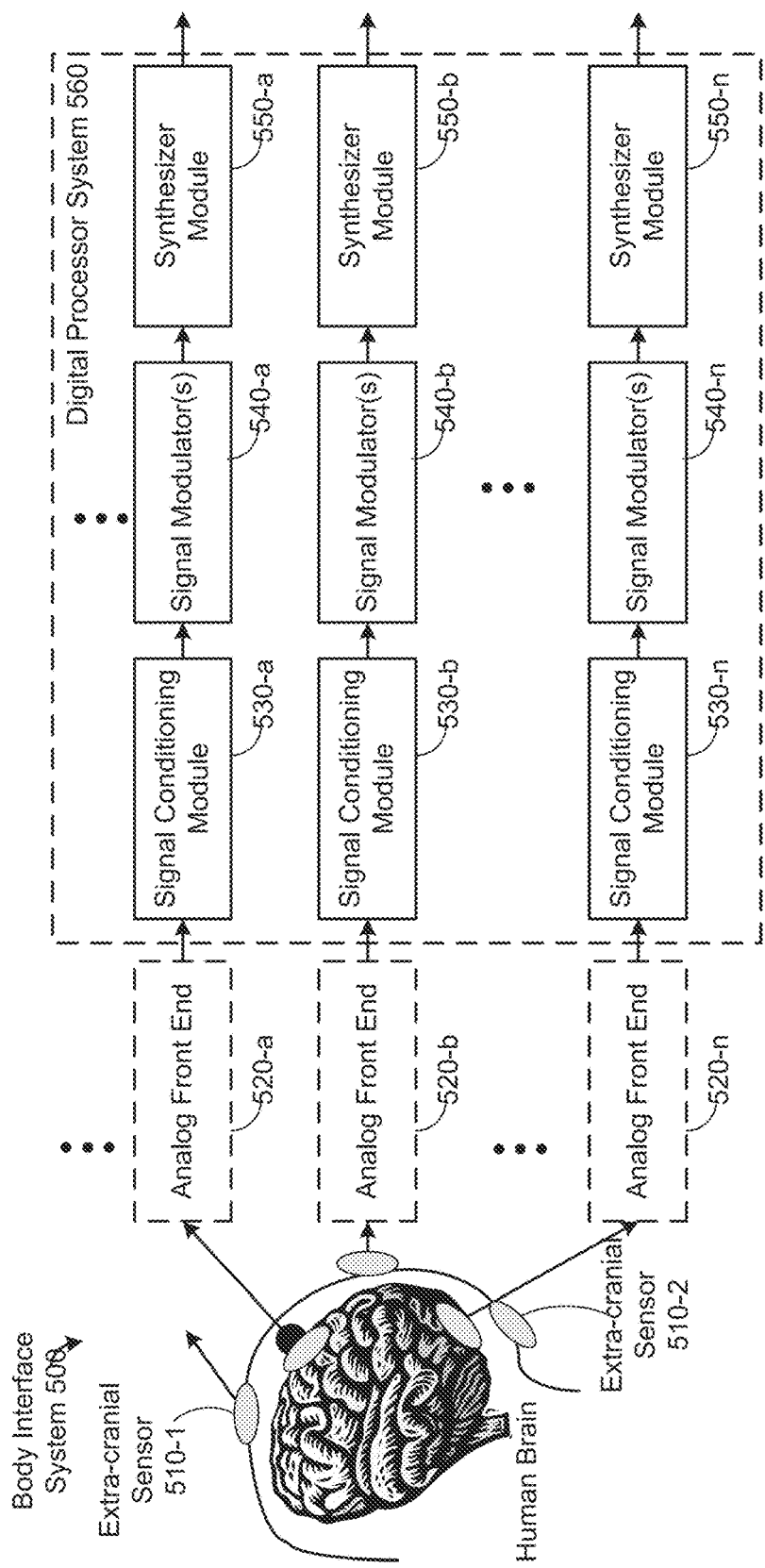
FIG. 5 illustrates a body interface system for acquiring and processing signals from a living subject, in accordance with some embodiments of the invention.

FIG. 5 illustrates body interface system 500 for sensing, acquiring and processing one or more signals obtained from a living subject (e.g., obtained from a human or animal's brain and/or heart) to produce a representation of an acoustic signal (also referred to herein as an "output acoustic signal") corresponding to the one or more signals (e.g., representing brain and/or heart activity). In some circumstances, body interface system 500 is deployed in a clinical setting (e.g., during or before surgical interventions and/or during diagnosis and/or treatment of conditions, such as epileptic seizures) for aural (e.g., auditory) measurement or monitoring of brain activity. Alternatively, or in addition, body interface system 500 is deployed as part of a user interface for a handheld or wearable device (e.g., a smart-phone, tablet, or the like) for diagnostic, entertainment, biofeedback, monitoring, therapeutic or other purposes. In some embodiments, one or more components of body interface system 500 constitute a handheld or wearable device for sonifying electrical signals obtained from a subject. Three examples of handheld devices for sonifying electrical signals obtained from a subject are shown in FIGS. 9A-9C, FIGS. 10A-10B, and FIG. 11, respectively. An example of a wearable device for sonifying electrical signals obtained from a subject is shown in FIG. 11. In some implementations of the wearable device, shown in FIG. 11, digital processor system 560 is embedded in the wearable device, for example in a "headband housing" that also holds dry or wet electrodes that contact both sides (left and right sides) of the subject's head. In some other implementations, digital processor system 560 is not embedded in a headband housing, and is instead coupled to electrodes in (or held in position by) a headband by one or more electrical wires or connectors. Optionally, digital processor system 560 has a separate housing that includes a clip for attachment to the headband.

In some embodiments, as shown in FIG. 5, body interface system 500 includes one or more sensors 510 (e.g., sensor 510-1 and sensor 510-2), optionally includes one or more analog front ends 520 (e.g., one or more analog front end modules) and a digital processor system 560 (herein often called digital processor 560 for ease of reference) for receiving and processing signals from sensors 510. In some embodiments, digital processor system 560 includes the one or more analog front ends.

In some embodiments, sensors 510 are provided to interface with a living subject's brain to obtain (e.g., sense and/or acquire) sensor time-domain signals (e.g., sensor time-domain signal 601, FIG. 6A) corresponding to brain electrical activity. In some embodiments, sensors 510 are a component of a handheld or wearable device for sonifying electrical signals (see FIGS. 9A-9C through 8A-1B). Alternatively, in some embodiments, the handheld or wearable device is configured to interface with the sensors 510 (e.g., the sensors 510 are disposable and plug into the handheld or wearable device). In some embodiments, the sensors 510 include one or more electrodes.

As an example, signals (e.g., sensor time-domain signal 601, FIG. 6A) corresponding to brain electrical activity are obtained from a human brain and correspond to electrical signals obtained from a single neuron or from a plurality of neurons. In some embodiments, the one or more electrical signals represent electroencephalography (EEG) data that are concordant with laboratory EEG data. In some embodiments, sensors 510 include one or more sensors affixed (e.g., taped, attached, glued) externally to a human scalp (e.g., extra-cranial sensor 510-1). For example, extra-cranial sensor 510-1 includes an electrode (e.g., electroencephalography (EEG) electrode) or a plurality of electrodes (e.g., electroencephalography (EEG) electrodes) affixed externally to the scalp (e.g., glued to the skin via conductive gel), or more generally positioned at respective positions external to the scalp. Alternatively, dry electrodes can be used in some implementations (e.g., conductive sensors that are mechanically placed against a living subject's body rather than implanted within the living subject's body or held in place with a conductive gel). An example of a dry-electrode is a headband with one or more metallic sensors (e.g., electrodes) that is worn by the living subject during use (FIG. 11). The signals obtained from an extra-cranial sensor 510-1 are sometimes herein called EEG signals or time-domain EEG signals.

In some embodiments, although not shown in FIG. 5, sensors 510 are heartbeat pulse sensors. In some embodiments, sensors 510 can be used both as EEG sensors (e.g., by placing sensors 510 on the subject's head) and as heartbeat pulse sensors (e.g., by placing sensors 510 on the subject's chest or another location where a heart signal is detectable). The heartbeat pulse sensors are provided to interface with a living subject's heart to obtain (e.g., sense and/or acquire) sensor time-domain signals corresponding to heart electrical activity. For example, signals corresponding to heart electrical activity are obtained from a human heart and correspond to electrical signals obtained from a single cardiomyocyte or from a plurality of cardiomyocytes (e.g., a sinoatrial (SA) node of a human subject). In some embodiments, the heartbeat pulse sensors include one or more sensing elements affixed (e.g., taped, attached, glued) externally to a human body (e.g., a human subject's chest, abdomen, arm, or leg). For example, the heartbeat pulse sensors include an electrode (e.g., electrocardiography (ECG) electrode) or a plurality of electrodes (e.g., electrocardiography (ECG) electrodes) affixed externally to the human body (e.g., glued to the skin via conductive gel), or more generally positioned at respective positions external to the human body. Alternatively, dry electrodes can be used in some implementations (e.g., conductive sensors that are mechanically placed against a human body rather than being implanted within the human body or held in place with a conductive gel). An example of a dry-electrode is a chest strap with one or more metallic sensors (e.g., electrodes) that is worn by the living subject during use. Another example of a dry-electrode is a thumb apparatus or a hand apparatus with one or more metallic sensing elements (e.g., electrodes) that is touched (e.g., with the living subject's thumbs) and/or held onto (e.g., with the living subject's hands) by the living subject during use. The signals obtained from heartbeat pulse sensors are sometimes herein called ECG signals or time-domain ECG signals.

In some embodiments, heartbeat pulse sensors sense voltages corresponding to heart electrical activity. In alternative embodiments, heartbeat pulse sensors sense electrical currents corresponding to heart electrical activity. In some implementations, heartbeat pulse sensors sense differential voltages (e.g., differences in voltage values) between two measurement locations (e.g., between two sensing elements). For example, when a respective heartbeat pulse sensor includes two or more sensing elements (e.g., electrodes) positioned at respective positions external to the human body, the respective heartbeat pulse sensor senses differential voltages (e.g., bipolar voltages) between the two or more sensing elements located at the respective positions. In some implementations, a "twelve-lead electrocardiogram" is constructed by referencing each sensing element of a set of sensing elements to one or more other sensing elements to produce a corresponding set of differential voltage signals (e.g., a twelve-lead set of differential voltage signals), each of which is a respective sensor time-domain signal 601 (FIG. 6A).

Figure 6A:
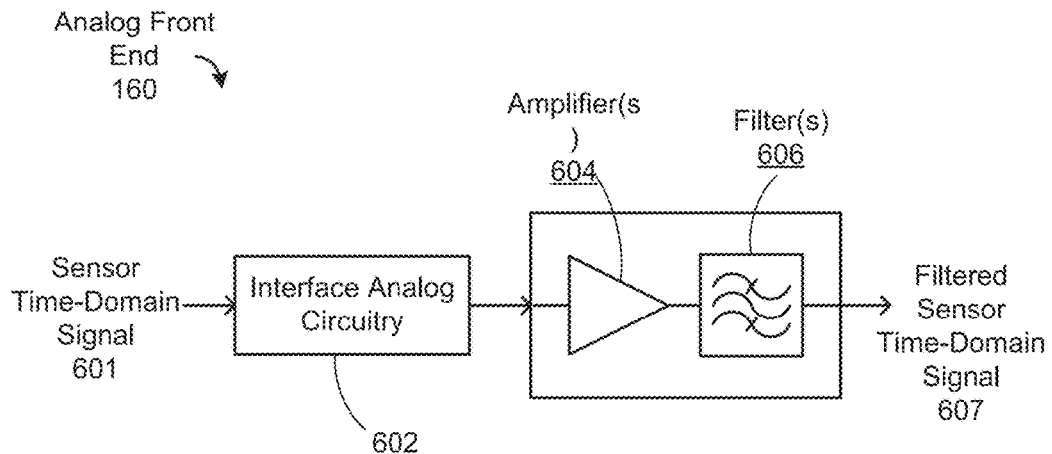
FIG. 6A is a block diagram illustrating an analog front end used for pre-processing electrical signals obtained from a living subject, in accordance with some embodiments of the invention.

In some embodiments, arrays of sensors (e.g., sensors 510) are designed to record intracranial EEG and produce a plurality of sensor time-domain signals (e.g., sensor time-domain signals 601, FIG. 6A). In some embodiments, sensor time-domain signals (e.g., sensor time-domain signal 601, FIG. 6A) include wideband features including high-gamma bursts in the range of 80-150 Hz. In some embodiments, sensor time-domain signals (e.g., sensor time-domain signal 601, FIG. 6A) include frequencies (sometimes called frequency components) below (e.g., lower than or in the lowest ranges of) the human audible frequency-range.

In some implementations, analog front end 520 receives sensor time-domain signals (e.g., sensor time-domain signal 601, FIG. 6A) from sensors 510 and optionally pre-processes the sensor time-domain signals to produce filtered sensor time-domain signals (e.g., filtered sensor time-domain signals 607, FIG. 6A). In some embodiments, a separate (e.g., independent) analog front end is provided for interfacing with each of a set of sensors 510. In some embodiments, a first analog front end is provided for interfacing with a set of EEG sensors 510, and a second (i.e., distinct) electrocardiography (ECG) analog front end is provided for interfacing with a set of heartbeat pulse sensors 510. In such embodiments, body interface system 500 comprises a plurality of analog front end modules (e.g., analog front end 520-*a*, analog front end 520-*b*, through analog front end 520-*n*) for interfacing with a plurality of sensors 510.

As shown in FIG. 5, body interface system 500 includes digital processor system 560 for processing signals obtained from the living subject (e.g., signals corresponding to electrical activity of the brain or heart), optionally after the signals are pre-processed by analog front end 520. Digital processor 560 includes signal conditioning modules 530, signal modulators 540, and synthesizer modules 550. In some embodiments, a separate (e.g., independent) signal conditioning module, a separate (e.g., independent) signal modulator, and/or a separate (e.g., independent) synthesizer module is provided for interfacing with each sensor 510 in a set of two or more sensors 510 (optionally through a separate analog front end module). In such embodiments, body interface system 500 comprises a plurality of signal conditioning modules (e.g., signal conditioning module 530-a, signal conditioning module 530-b, through signal conditioning module 530-n), a plurality of signal modulators (e.g., signal modulators 540-a, signal modulators 540-b, through signal modulators 540-n), and/or a plurality of synthesizer modules (e.g., synthesizer module 550-a, synthesizer module 550-b, through synthesizer module 550-n) for interfacing with a plurality of sensors 510 and processing signals obtained from those sensors.

In some embodiments, a respective signal conditioning module 530 includes a data converter (e.g., an analog-to-digital converter for converting an analog filtered sensor time-domain signal obtained from sensors 510 to a corresponding digital representation), an up-sampler and a digital low-pass filter. In some implementations, signal modulators 540 receive the digitized time-domain signals output by signal conditioning modules 530, and concurrently generate a set of acoustic parameters, including a plurality of time-varying acoustic parameters from (e.g., using) the digitized time-domain signals. One or more of the plurality of time-varying acoustic parameters is modulated in accordance with at least the signal value of the time-domain signal (e.g., time-domain signal 618, FIG. 6B, produced by signal conditioning module 530). In some embodiments, synthesizer module (e.g., synthesizer module 550) combines the concurrently generated set of acoustic parameters to produce a representation of an acoustic signal corresponding to the time-domain signal (e.g., time-domain signal 618, FIG. 6B, produced by signal conditioning module 530). As used herein, the term "representation of an acoustic signal" can be exchanged synonymously with the term "output acoustic signal".

In some embodiments, a plurality of representations of acoustic signals is combined to produce a combined acoustic signal. Alternatively, a combined acoustic signal is generated by combining acoustic signals corresponding to the plurality of representations of acoustic signals produced by digital processor system 560. In yet another alternative, a plurality of acoustic signals, each corresponding to one or more of the aforementioned representations of acoustic signals, are recorded on distinct tracks, where the distinct tracks are configured to enable concurrent playback of the acoustic signals recorded in those tracks.

FIG. 6A illustrates a block diagram of an analog front end (e.g., analog front end 520, FIG. 5) optionally included in body interface system 500. In some embodiments, analog front end 520 receives a sensor time-domain signal (e.g., sensor time-domain signal 601) from a respective sensor 510 and pre-processes the sensor time-domain signal to produce a filtered sensor time-domain signal (e.g., filtered sensor time-domain signal 607). When body interface system 500 includes a plurality of analog front ends 520, the analog front ends 520 process a corresponding number of sensor time-domain signals in parallel to produce filtered sensor time-domain signals.

In some embodiments, analog front end 520 includes interface circuitry (e.g., interface analog circuitry 602) to interface with a respective sensor 510, for example, by way of providing bias voltages and/or currents to the respective sensor 510, buffering signals (e.g., using a buffer amplifier) received from sensors 510 and/or providing appropriate coupling conditions (e.g., providing appropriate input impedance) for interfacing with the signals received from sensors 510.

Alternatively, or in addition, according to some implementations, analog front end 520 includes one or more amplifiers 604 and/or filters 606 to pre-process (e.g., amplify and/or filter) sensor time-domain signals corresponding to brain electrical activity or heart electrical activity (e.g., sensor time-domain signal 601, FIG. 6A) obtained (e.g., sensed and/or acquired) from one or more sensors 510. As noted above, in some embodiments, analog front end 520 produces a filtered sensor time-domain signal (e.g., filtered sensor time-domain signal 607).

Figure 6B:
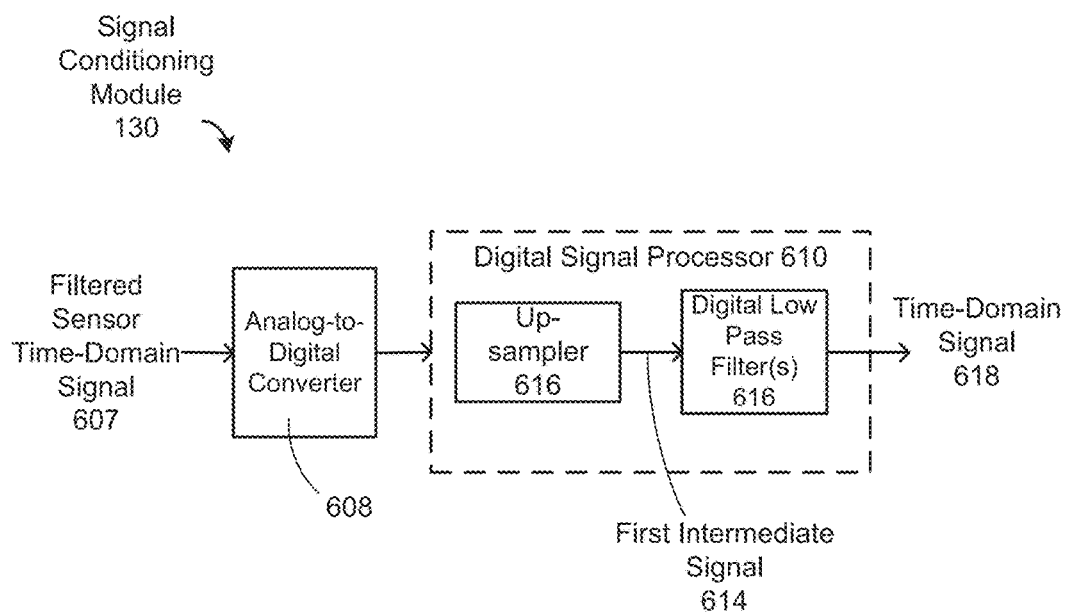
FIG. 6B is a block diagram illustrating a signal conditioning module used for processing electrical signals obtained from a living subject, in accordance with some embodiments of the invention.

FIG. 6B illustrates a block diagram of a signal conditioning module (e.g., signal conditioning module 530) included in body interface system 500. As shown in FIG. 6B, signal conditioning module 530 receives filtered sensor time-domain signals (e.g., filtered sensor time-domain signal 607)—optionally obtained after pre-processing by analog front end 520—and conditions the filtered sensor time-domain signals to produce conditioned time-domain signals (e.g., time-domain signal 618).

In some embodiments, the signal conditioning module (e.g., signal conditioning module 530) includes a data converter (e.g., analog-to-digital converter 608) for converting an analog filtered sensor time-domain signal obtained from sensors 510 (optionally after pre-processing by analog front end 520) to a corresponding digital representation with a predefined sampling rate (e.g., a sampling rate between 500 Hz and 2 kHz, such as 500 Hz; or more generally a sampling rate between 800 Hz to 4 kHz). Signal conditioning module 530 includes an up-sampler (e.g., up-sampler 612) to up-sample (e.g., increase the sampling rate of) the digital representation of the analog filtered sensor time-domain signal to produce a first intermediate signal (e.g., first intermediate signal 614). In some embodiments, the digital representation of the analog filtered sensor time-domain signal is up-sampled to produce a first intermediate signal having an audio sampling rate, for example, a sampling rate (e.g., 48 kHz) used in conventional audio applications. In some implementations, the first intermediate signal (e.g., first intermediate signal 614) produced by up-sampler 612 has a sampling rate of 48 kHz.

In some implementations, signal conditioning module 530 includes one or more digital low-pass filters (e.g., digital low pass filter 616) for filtering first intermediate signal 614 so as to produce time-domain signal 618. In some implementations, digital low pass filter 616 is a second order low-pass Butterworth filter with a 250 Hz corner frequency (also called a cutoff frequency). Digital low pass filter 616 filters first intermediate signal 614 to produce time-domain signal 618. In some embodiments, up-sampler 612 and digital low pass filter 616 are implemented in digital signal processor 610, sometimes called a DSP. In some other implementations, up-sampler 612 and digital low pass filter 616 are implemented in circuitry. Alternatively, up-sampler 612 and digital low pass filter 616 are implemented in software executed by a general purpose processor. Without limitation, it is noted that up-sampling and then low pass filtering the digital representation of the analog filtered sensor time-domain signal may be used to convert the output of one or more sensors (e.g., extra-cranial sensors and/or heartbeat/pulse sensors) to a form that is suitable for use with a music or other audio synthesizer, while removing or limiting artifacts produced by the conversion process.

Figure 6C:
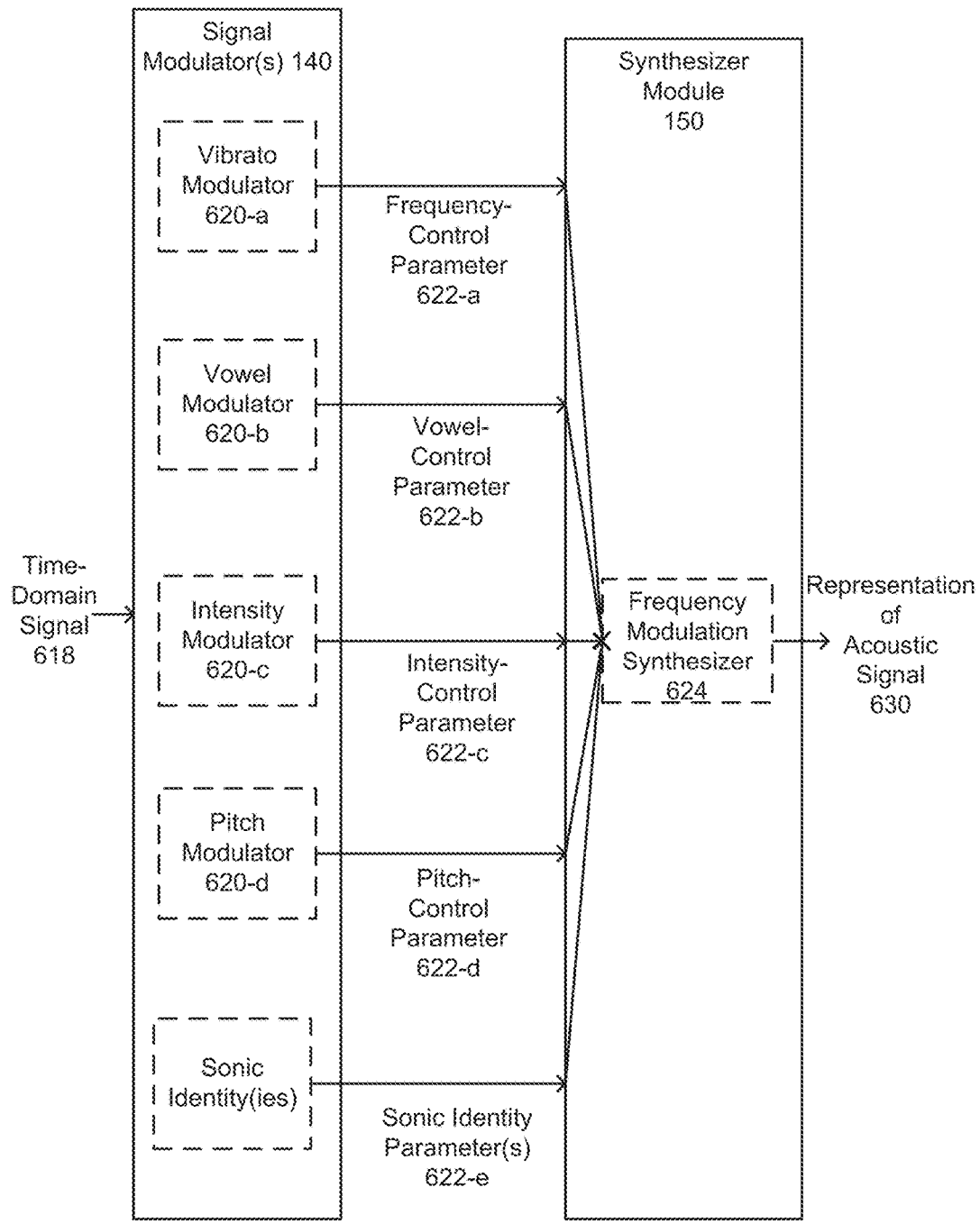
FIG. 6C is a block diagram illustrating signal modulators and a synthesizer module used for processing electrical time-domain signals obtained from a living subject to produce a representation of an acoustic signal, in accordance with some embodiments of the invention.

FIG. 6C illustrates a block diagram of signal modulator 540 and synthesizer module 550. Signal modulators 540 receive time-domain signals 618 from signal conditioning modules 530 (as explained above with reference to FIG. 6B). Signal modulators 540 generate at least one time-varying acoustic parameter corresponding to a respective time-domain signal 618. In some embodiments, signal conditioning modules 530 concurrently generate a set of acoustic parameters, including a plurality of time-varying acoustic parameters. In some embodiments, the plurality of acoustic parameters includes a frequency-control parameter (e.g., frequency-control parameter 622-a). In some embodiments, the plurality of acoustic parameters includes a vowel-control parameter (e.g., vowel-control parameter 622-b). In some embodiments, the plurality of acoustic parameters includes a time-varying intensity-control parameter (e.g., intensity-control parameter 622-c). In some embodiments, the set of acoustic parameters includes a pitch-control parameter (e.g., pitch-control parameter 622-d). In some embodiments, the set of acoustic parameters includes one or more sonic identity parameters (e.g., sonic identity parameters 622-e).

In some embodiments, signal modulator 540 includes a vibrato modulator (e.g., vibrato modulator 620-a) which generates a vibrato or frequency-control parameter (e.g., frequency-control parameter 622-a). In some implementations, the vibrato modulator (e.g., vibrato modulator 620-a) obtains a base frequency or pitch (e.g., a base frequency such as 50 Hz, 500 Hz, or any suitable frequency in the range of 50 Hz to 4 kHz) and modulates the base frequency in accordance with the signal value (e.g., amplitude, intensity and/or power) of the time-domain signal (e.g., time-domain signal 618). In other implementations, the vibrato modulator generates a vibrato or frequency-control parameter in accordance with the signal value of the time-domain signal (e.g., time-domain signal 618) that does not incorporate the base frequency or pitch. The amount of vibrato, as represented by the vibrato or frequency-control parameter, controls variations in frequency in the synthesized audio signal (i.e., the representation of an acoustic signal corresponding to the time-domain signal).

In some embodiments, signal modulator 540 includes a vowel modulator (e.g., vowel modulator 620-b) which generates a vowel-control parameter (e.g., vowel-control parameter 622-b). In some implementations, a vowel modulator (e.g., vowel modulator 620-b) selects a sequence of acoustic waveform patterns from a set of N (e.g., N is an integer in the range of 2 to 15, such as N=12) acoustic waveform patterns comprising a sequence of phoneme waveform patterns (e.g., phoneme patterns corresponding to sounds in spoken language). In some implementations, the phoneme patterns include a plurality of vowel waveform patterns, and optionally include phoneme patterns that are not vowel waveform patterns (e.g., "sss" or "vvv"). In some implementations, each of the phoneme patterns is distinguished from the other phoneme waveform patterns in the set with respect to acoustic characteristics such as formants. In some embodiments, vowel modulator (e.g., vowel modulator 620-b) modulates a rate at which the acoustic waveform (e.g., vowel waveform) patterns are sequentially selected in accordance with the signal value (e.g., amplitude, intensity and/or power) of the time-domain signal. For example, vowel modulator (e.g., vowel-control parameter 622-b) modulates a rate at which acoustic waveform patterns from a set of 12 acoustic waveform patterns are sequentially selected in accordance with the signal value (e.g., amplitude) of the time-domain signal (e.g., time-domain signal 618). For example, an increase in signal value (e.g., amplitude) of the time-domain signal (e.g., time-domain signal 618), causes vowel modulator (e.g., vowel-control parameter 622-b) to sequentially select acoustic waveform patterns from a set of 12 acoustic waveform patterns more rapidly or at an increased rate; and conversely, a decrease in signal value (e.g., amplitude) of the time-domain signal (e.g., time-domain signal 618), causes vowel modulator (e.g., vowel-control parameter 622-b) to sequentially select acoustic waveform patterns from a set of 12 acoustic waveform patterns more gradually (e.g., slowly) or at a decreased rate.

In some embodiments, signal modulator 540 includes an intensity modulator (e.g., intensity modulator 620-c) which generates an intensity-control parameter (e.g., intensity-control parameter 622-c). For example, an intensity modulator (e.g., intensity modulator 620-c) computes a time-varying amplitude value in accordance with the signal value (e.g., amplitude, intensity, and/or power) of the time-domain signal (e.g., time-domain signal 618) and generates a time-varying intensity-control parameter (e.g., intensity-control parameter 622-c) corresponding to the computed time-varying amplitude value. In some implementations, an increase in signal value (e.g., amplitude) of the time-domain signal (e.g., time-domain signal 618), causes the time-varying amplitude value—and corresponding time-varying intensity-control parameter (e.g., intensity-control parameter 622-c)—computed by intensity modulator (e.g., intensity modulator 620-c) to increase. Conversely, a decrease in signal value of the time-domain signal (e.g., time-domain signal 618), causes the time-varying amplitude value—and corresponding time-varying intensity-control parameter (e.g., intensity-control parameter 622-c)—computed by intensity modulator (e.g., intensity modulator 620-c) to decrease.

In some embodiments, signal modulator 540 includes a pitch modulator (e.g., pitch modulator 620-d) which generates a pitch-control parameter (e.g., pitch-control parameter 622-d). In some embodiments, pitch modulator (e.g., pitch modulator 620-d) selects a base frequency (e.g., corresponding to an acoustic pitch) in accordance with a spatial location of sensing the time-domain signal. In some embodiments, pitch modulator (e.g., pitch modulator 620-d) generates a time-varying pitch-control parameter in accordance with the selected base frequency and the signal value (e.g., amplitude, intensity and/or power) of the time-domain signal (e.g., time-domain signal 618, FIG. 6B). For example, pitch modulator (e.g., pitch modulator 620-d) selects a base frequency (e.g., a pitch) in accordance with a spatial location in the brain of sensing (e.g., by way of sensors 510 located at different spatial locations in the brain) of the time-domain signal (e.g., sensor time-domain signal 601, FIG. 6A). For example, for a time-domain signal obtained from the left hemisphere in the brain, pitch modulator (e.g., pitch modulator 620-d) selects a lower base frequency (e.g., a frequency corresponding to the pitch of baritone voice); for a time-domain signal obtained from the right hemisphere in the brain, pitch modulator (e.g., pitch modulator 620-d) selects a higher base frequency (e.g., a frequency corresponding to the pitch of a tenor voice); and for a time-domain signal obtained from the heart, pitch modulator (e.g., pitch modulator 620-d) selects a still higher base frequency (e.g., a frequency corresponding to the pitch of a soprano voice). More generally, in some implementations, when more than one time-domain signal is obtained from distinct sensors on a human body (e.g., distinct extra-cranial sensors and/or distinct ECG sensors), each time-domain signal is assigned a distinct base frequency so as to enable a listener to distinguish between the "voices" (acoustic signals or acoustic signal portions) corresponding to the distinct sensors and their time-domain signals.

In some embodiments, signal modulator 540 generates, obtains or otherwise provides one or more sonic identity parameters 622-*e*. In some embodiments, signal modulators 540 selects a sonic identity (for example, specific defining acoustic characteristics; e.g., acoustic characteristics associated with specific musical instruments) in accordance with a respective time-domain signal (e.g., a time-domain signal corresponding to a spatial location in the brain of sensing or a spatial location in the heart of sensing by way of sensors 510 located at different spatial locations in the brain and heart, respectively) and generates, obtains or otherwise provides one or more sonic identity parameters 622-*e* in accordance with the selected sonic identity. For example, for a time-domain signal obtained from the left hemisphere in the brain (e.g., obtained from sensors 510-5, 510-6 in FIG. 11), signal modulator 540 selects a sonic identity corresponding to the sonic identity of (e.g., acoustic characteristics defining or associated with) a violin; for a time-domain signal obtained from the right hemisphere in the brain (e.g., obtained from sensors 510-7, 510-8 in FIG. 11), signal modulator 540 selects a sonic identity corresponding to the sonic identity of (e.g., acoustic characteristics defining or associated with) a guitar; and for a time-domain signal obtained from the heart (obtained from sensors not shown in the Figures, but sometimes obtained as sensors on a chest strap), signal modulator 540 selects a sonic identity corresponding to the sonic identity of (e.g., acoustic characteristics defining or associated with) a clarinet. More generally, in some implementations, when more than one time-domain signal is obtained from distinct sensors on a human body, each time-domain signal is assigned a distinct sonic identity (e.g., and a corresponding set of one or more sonic identity parameters 622-*e*), so as to enable a listener to distinguish between the "voices" (acoustic signals or acoustic signal portions) corresponding to the distinct sensors and their time-domain signals.

One or more of the plurality of time-varying acoustic parameters (e.g., frequency-control parameter 622-*a*, vowel-control parameter 622-*b*, and/or intensity-control parameter 622-*c*) are modulated in accordance with at least the signal value (e.g., amplitude, intensity, and/or power) of the time-domain signal (e.g., time-domain signal 618, FIG. 6B, produced by signal conditioning module 530).

A synthesizer module produces a representation of an acoustic signal from the one or more acoustic parameters corresponding to a respective time domain signal 618. In some embodiments, a synthesizer module (e.g., synthesizer module 550) combines the concurrently generated set of acoustic parameters (e.g., the acoustic parameters produced by signal modulators 540 described above) to produce a representation of an acoustic signal (e.g., representation of acoustic signal 630) corresponding to the time-domain signal (e.g., time-domain signal 618, FIG. 6B, produced by signal conditioning module 530). In some embodiments, synthesizer module 550 is a music synthesizer or a music synthesizer module, for example a frequency modulation synthesizer (e.g., frequency modulation synthesizer 624). In some embodiments, a frequency modulation synthesizer (e.g., frequency modulation synthesizer 624) uses frequency modulation synthesis, controlled by the concurrently generated set of acoustic parameters, to generate a representation of an acoustic signal 630. For example, the frequency modulation synthesizer (e.g., frequency modulation synthesizer 624) modifies the timbre (e.g., the quality) of a waveform by frequency modulating it with a modulating signal. With respect to frequency modulation synthesis, U.S. Pat. No. 4,018,121, "Method of synthesizing a musical sound" is hereby incorporated by reference in its entirety.

As shown in FIG. 5, in some embodiments, signal modulator 540 and/or synthesizer module 550 are implemented in digital processor 560. In some implementations, signal modulator 540 and/or synthesizer module 550 are implemented in a digital signal processor, sometimes called a DSP. In some implementations, signal modulator 540 and/or synthesizer module 550 are implemented in circuitry. And in some implementations, signal modulator 540 and/or synthesizer module 550 are implemented in software executed by a general purpose processor.

Figure 7A:
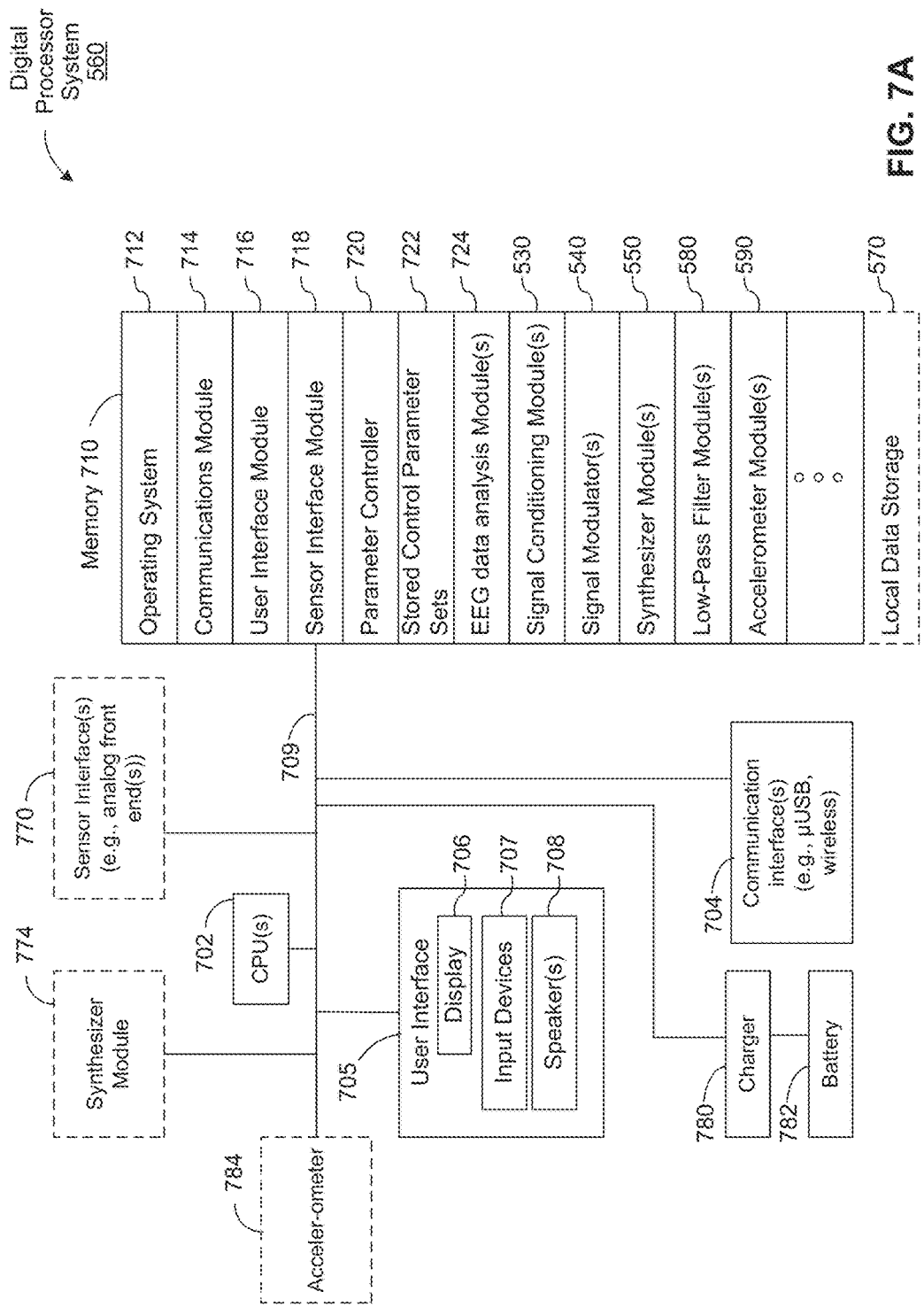
FIG. 7A is a block diagram illustrating a digital processor used for processing signals representing bodily functions, in accordance with some embodiments of the invention.
Figure 7B:
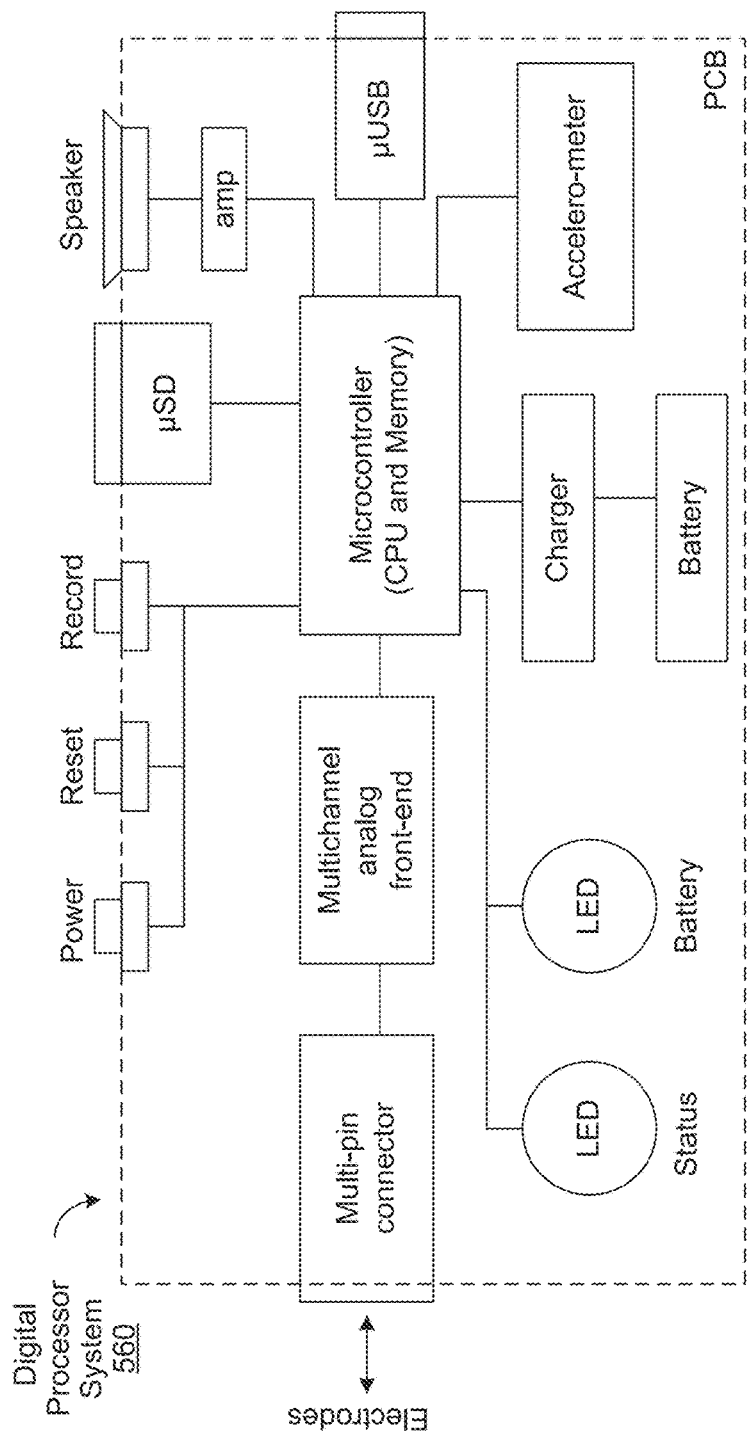
FIG. 7B is a schematic diagram of circuitry in a portable, pocket-sized handheld device for sonifying electrical signals, in accordance with some embodiments of the invention.

FIG. 7A is a block diagram illustrating digital processor system 560 in accordance with some embodiments, and FIG. 7B depicts an example of a set of components on a printed circuit board (PCB) that implement digital processor system 560. Digital processor system 560 typically includes one or more processing units (CPUs) 702 for executing modules, programs and/or instructions stored in memory 710 and thereby performing processing operations; one or more network or other communications interfaces 704 (e.g., a wired communication interface such as a USB port, micro-USB port, or the like, and/or a wireless communication interface); memory 710; and one or more communication buses 709 for interconnecting these components. The communication buses 709 optionally include circuitry (sometimes called a chipset) that interconnects and controls communications between system components. Digital processor system 560 optionally includes a user interface 705 comprising a display 706, one or more input devices 707 (e.g., one or more buttons, and, optionally, one or more of a microphone, keypad, and touch screen, etc.), and one or more speakers 708 (e.g., for audio playback of acoustic signals corresponding to brain and/or heart activity). Display 706 optionally includes one or more LEDs, for example one or more LEDs for indicating a status of digital processor system 560 (e.g., a steady blinking LED to indicate that EEG signals are being received and/or to indicate that accelerometer signals corresponding to mechanical movement of the subject are sufficiently low-amplitude to allow DSP 560 to produce valid sonification of EEG signals) and, in another example, an LED to indicate battery status (e.g., a red LED that is turned on when battery power is low, and/or a green LED that is turned on when an internal battery is charged and that blinks on and off in a predefined pattern when battery power is low).

As shown in FIG. 7B, in some embodiments, input devices 707 include a power on/off button for powering digital processor system 560 on and off, a reset button for resetting digital processor system 560 to a predefined initial state, and a record button for starting and stopping recording of EEG data corresponding to a subject's brain activity. Furthermore, in some embodiments, input devices 707 include a microphone for receiving and recording a user's spoken comments made just prior to, or while, DSP 560 recording EEG data corresponding to a subject's brain activity. For example, in response to a user pressing the "record" button shown in FIG. 7B, digital processor system 560 records any spoken comments by the user for a predefined period (e.g., 5 to 10 seconds following the button press), and also records EEG data corresponding to the subject's brain activity until the user presses the record button a second time, or until a predefined period of time elapses (e.g., 5 minutes), or until a predefined period of time (e.g., 5 minutes) elapses during which the device (digital processor system 560) does not receive electrical signals corresponding to abnormal brain activity.

Digital processor system 560 optionally includes sensor interfaces 770 for interfacing with sensors 510 (FIG. 5) and/or analog front end 520 (FIG. 5) and synthesizer module 774 for combining concurrently generated acoustic parameters to produce a representation of an acoustic signal (e.g., representation of acoustic signal 630, FIG. 6C) corresponding to one or more time-domain signals (e.g., time-domain signal 618, FIG. 6B). As explained in more detail below, in some embodiments sensors 510 are located, at least in part, within the same housing that holds digital processor system 560, while in some other embodiments, sensors 510 are located external to that housing and are coupled to digital processor system 560 via one or more electrical connectors and sensor interface(s) 770.

In some embodiments, sensor interface 770 includes an impedance detector that detects whether sensors 510 (e.g., electrodes) are attached to the subject. In some embodiments, when DSP 560 determines that the impedance looking into sensors 510 is below an impedance threshold, DSP 560 determines that sensors 510 are attached to the subject. On the other hand, when DSP 560 determines that the impedance looking into the sensors 510 is above the impedance threshold, DSP determines that sensors 510 are not attached to the subject (e.g., the circuit formed by DSP 560 and sensors 510 is an open circuit).

Digital processor system 560 optionally includes an accelerometer 784 (e.g., a 3-axis accelerometer) that measures mechanical movement of the subject and/or the device (e.g., produces one or more electrical signals corresponding to mechanical movement of the subject and/or device).

Digital processor system 560 optionally (and typically) includes a battery 782 (e.g., a rechargeable battery) and charger 780, to provide power to digital processor system 560 and enable operation of digital processor system 560 without connection to an external power source (except to charge battery 782). In some embodiments, battery 782 is charged, via charger 780, when an external power source is connected to system 560 via a USB port or micro-USB port of the device.

Memory 710 includes high-speed random access memory, such as DRAM, SRAM, DDR RAM or other random access solid state memory devices; and optionally includes non-volatile memory, such as one or more magnetic disk storage devices, optical disk storage devices, flash memory devices, or other non-volatile solid state storage devices. Memory 710 optionally includes one or more storage devices remotely located from the CPUs 702. Memory 710, or alternately the non-volatile memory devices within memory 710, comprises a non-transitory computer readable storage medium. In some embodiments, memory 710, or the computer readable storage medium of memory 710 stores the following programs, modules and data structures, or a subset thereof:

- Operating system 712 that includes procedures for handling various basic system services and for performing hardware dependent tasks;
- Network communication module 714 that is used for connecting digital processor system 560 to other computers via the one or more communication network interfaces 709 (wired or wireless) and one or more communication networks, such as the Internet, other wide area networks, local area networks, metropolitan area networks, and so on;
- User interface module 716 that receives commands from the user via one or more input devices 707 of user interface 705, generates user interface objects in display device 706, and optionally generates representations of signals corresponding to brain and/or heart activity, information corresponding to sensors and sensor interfaces, and information related to the configuration of body interface system 500 for display on display device 706;
- Parameter controller 720 that controls (e.g., executes instructions for) the generation of the set of acoustic parameters, including a plurality of time-varying acoustic parameters (such as a frequency-control parameter (sometimes called a vibrato parameter), a vowel-control parameter, an intensity-control parameter, a pitch-control parameter, and/or an identity-control parameter). Parameter controller 720 also interacts with sensor interfaces 770 to facilitate selection of parameters (e.g., any of the aforementioned parameters) and corresponding parameter values based on the sensors selected and sensor signals obtained (e.g., based on a spatial location in the brain and/or heart from which the time-domain signal is sensed). For example, sensor interface module 718 interfaces with parameter controller 720 to communicate a set of parameters, corresponding to one or more of pitch, vowel selection, vibrato, intensity (amplitude), and sonic identity parameter, selected in accordance the selected sensor, or in accordance with a spatial location in the brain and/or heart of sensing a time-domain signal;
- Stored control parameter sets 722 that include one or more sets of signal parameters or values corresponding to signal parameters (for example, one or more values of base frequencies, a set of acoustic waveform patterns corresponding to phoneme patterns, one or more sonic identities, etc.);
- Signal conditioning modules 530 up-sample and low pass filter the sensor time-domain signal to produce a time-domain signal representing brain and/or heart activity;
- Signal modulators 540 concurrently generate a set of acoustic parameters, including a plurality of time-varying acoustic parameters, for example, a frequency-control parameter (e.g., frequency-control parameter 622-*a*, FIG. 6C), a vowel-control parameter (e.g., vowel-control parameter 622-*b*, FIG. 6C), a time-varying intensity-control parameter (e.g., intensity-control parameter 622-*c*, FIG. 6C), a pitch-control parameter (e.g., pitch-control parameter 622-*d*, FIG. 6C), and/or an sonic identity parameter (e.g., sonic identity parameters 622-*e*, FIG. 6C);
- Synthesizer modules 550 combine the concurrently generated set of acoustic parameters to produce a representation of an acoustic signal (e.g., representation of acoustic signal 630, FIG. 6C) corresponding to the time-domain signal (e.g., time-domain signal 618, FIG. 6B, produced by signal conditioning module 530);
- Low-pass filter modules 580 configure and/or apply a low-pass filter to electrical signals received from sensor interface 770 to remove electrical noise that results from convulsive muscle movements (e.g., low-pass filter module applies a fixed-configuration low-pass filter, or a low-pass filter configured by system 560 (as discussed in more detail below), or a user-selectable low-pass filter, which is in addition to the low-pass filter applied by signal conditioning module 530);
- Accelerometer modules 590 process accelerometer information from accelerometer 784 and optionally configure and/or apply filters to remove mechanical movement artifacts in electrical signals received from sensor interface 770; and Optional local data storage 570 that stores data corresponding to the one or more electrical signals (e.g., data storage 570 stores raw EEG data and/or audio data so that the data can be reviewed later by, e.g., a specialist). In some implementations, data storage 570 includes a removable non-volatile memory card, such as a micro SD flash memory card (see "pSD" in FIG. 7B, which represents a micro-SD card "reader" for receiving and interfacing a micro SD flash memory card to a microcontroller). As an alternative, or in addition to data storage 570, digital processor system 560 communicates with cloud-based storage (e.g., storage that is remote from the device) to store data corresponding to the one or more electrical signals.

Each of the above identified elements is optionally stored in one or more of the previously mentioned memory devices of digital processor system 560, and corresponds to a set of instructions for performing a function described above. The above identified modules or programs (i.e., sets of instructions) need not be implemented as separate software programs, procedures or modules, and thus various subsets of these modules is optionally combined or otherwise re-arranged in various embodiments. In some embodiments, memory 710 optionally stores a subset of the modules and data structures identified above. Furthermore, memory 710 optionally stores additional modules and data structures not described above. For example, in some embodiments, memory 710 stores one or more EEG data analysis modules 724, for analyzing EEG data received by digital processor system 560 and conveying one or more results to a user of the device (e.g., via display 706 or speaker(s) 708), or to a remote device or user via communications interface 704. The one or more EEG data analysis modules 724, if provided, may use any of a number of seizure detection methods, including EEG data analysis methods previously developed or developed in the future.

Although FIGS. 7A-7B show "digital processor system 560," FIGS. 7A-7B are intended to provide functional descriptions of the various features which are optionally present in a digital processor system, and not as a structural schematic of the embodiments described herein. In practice, and as recognized by those of ordinary skill in the art, items shown separately could be combined and some items could be separated. For example, some items shown separately in FIGS. 7A-7B could be implemented on a single digital processor system and single items could be implemented by one or more digital processor systems. The actual number of digital processor systems used to implement digital processor system 560 and how features are allocated among them will vary from one implementation to another.

D. Further Sonification Methods

Figure 8A:
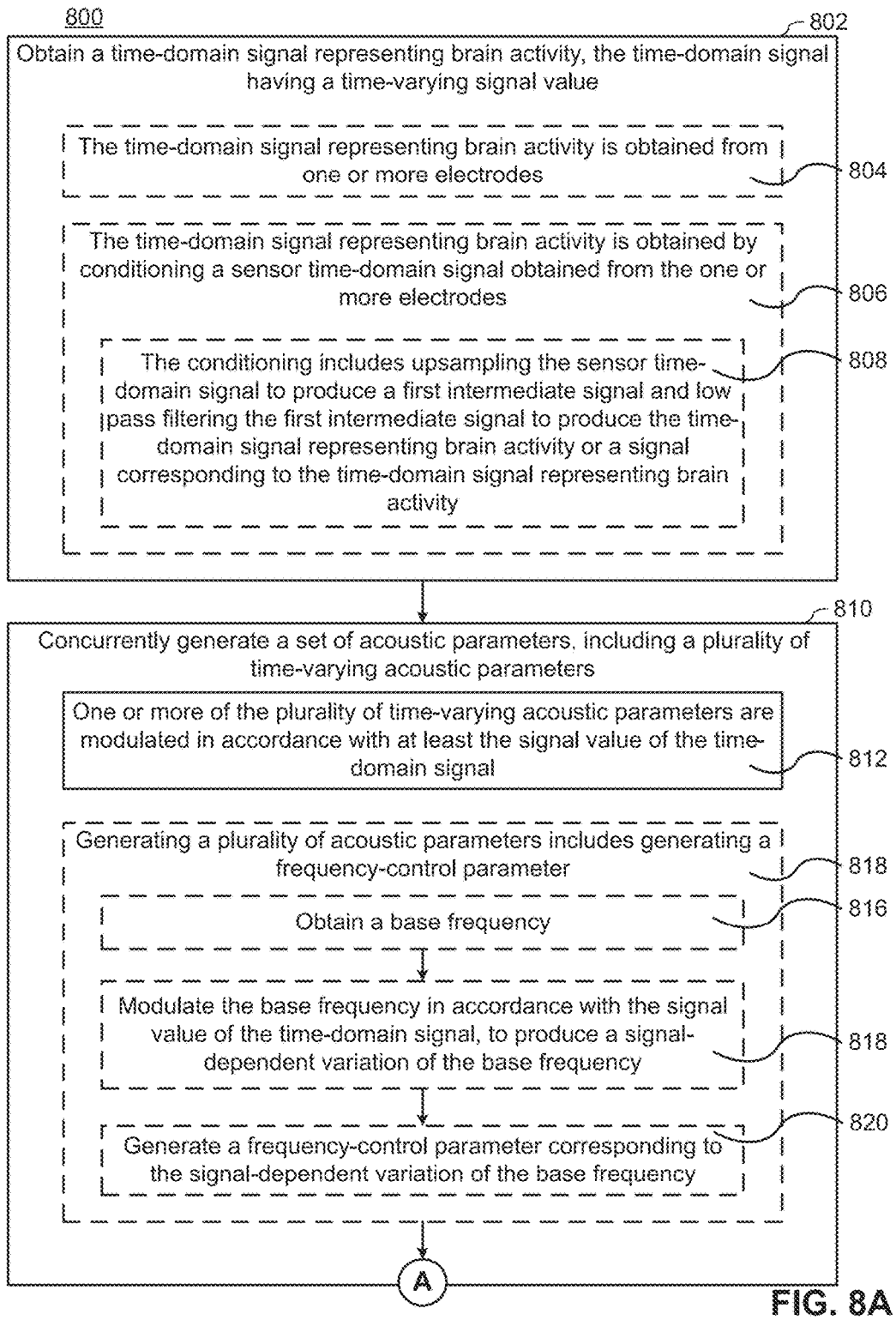
FIGS. 8A-8C include a flow chart illustrating a method for sonifying brain electrical activity, in accordance with some embodiments of the invention.
Figure 8B:
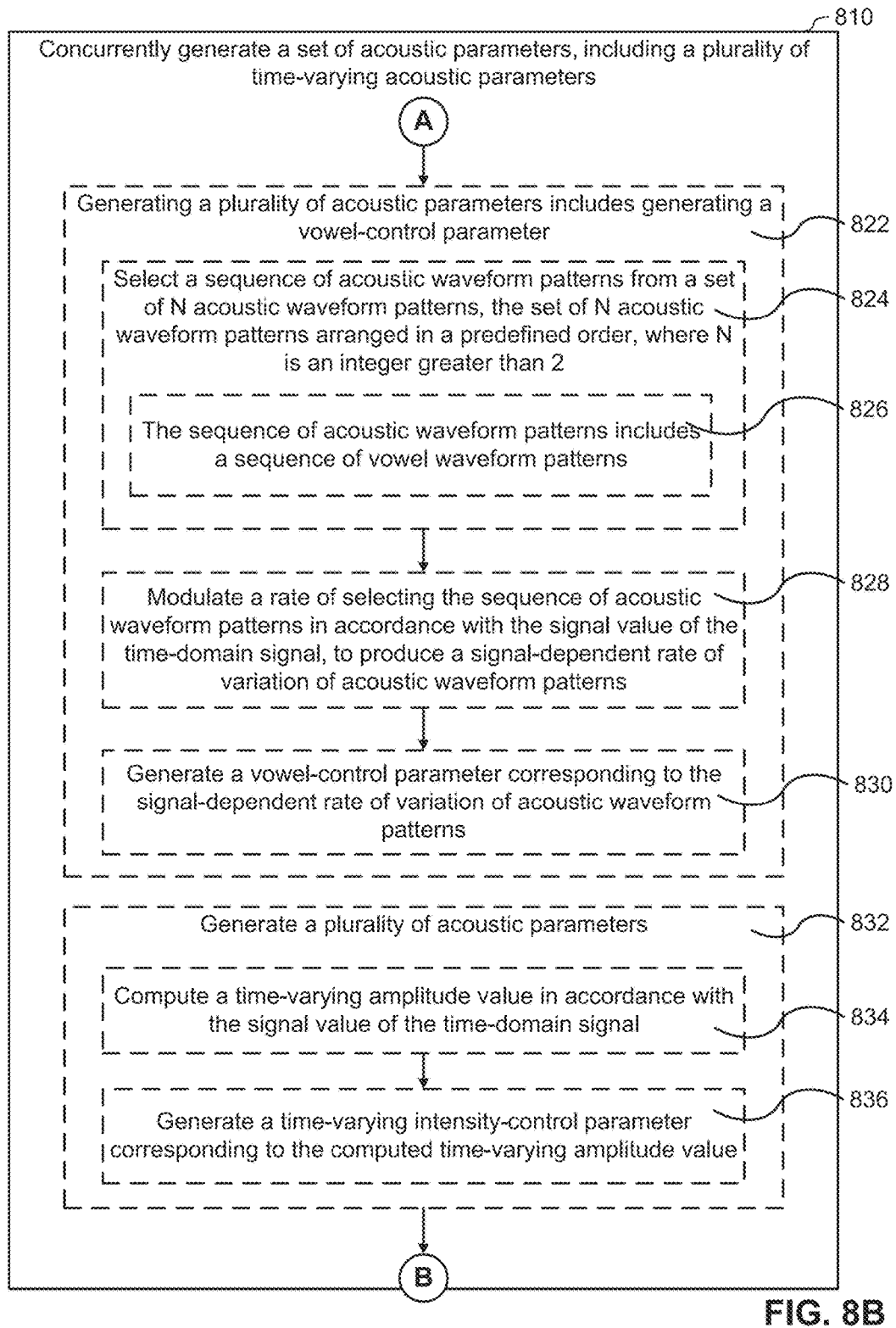
Figure 8C:
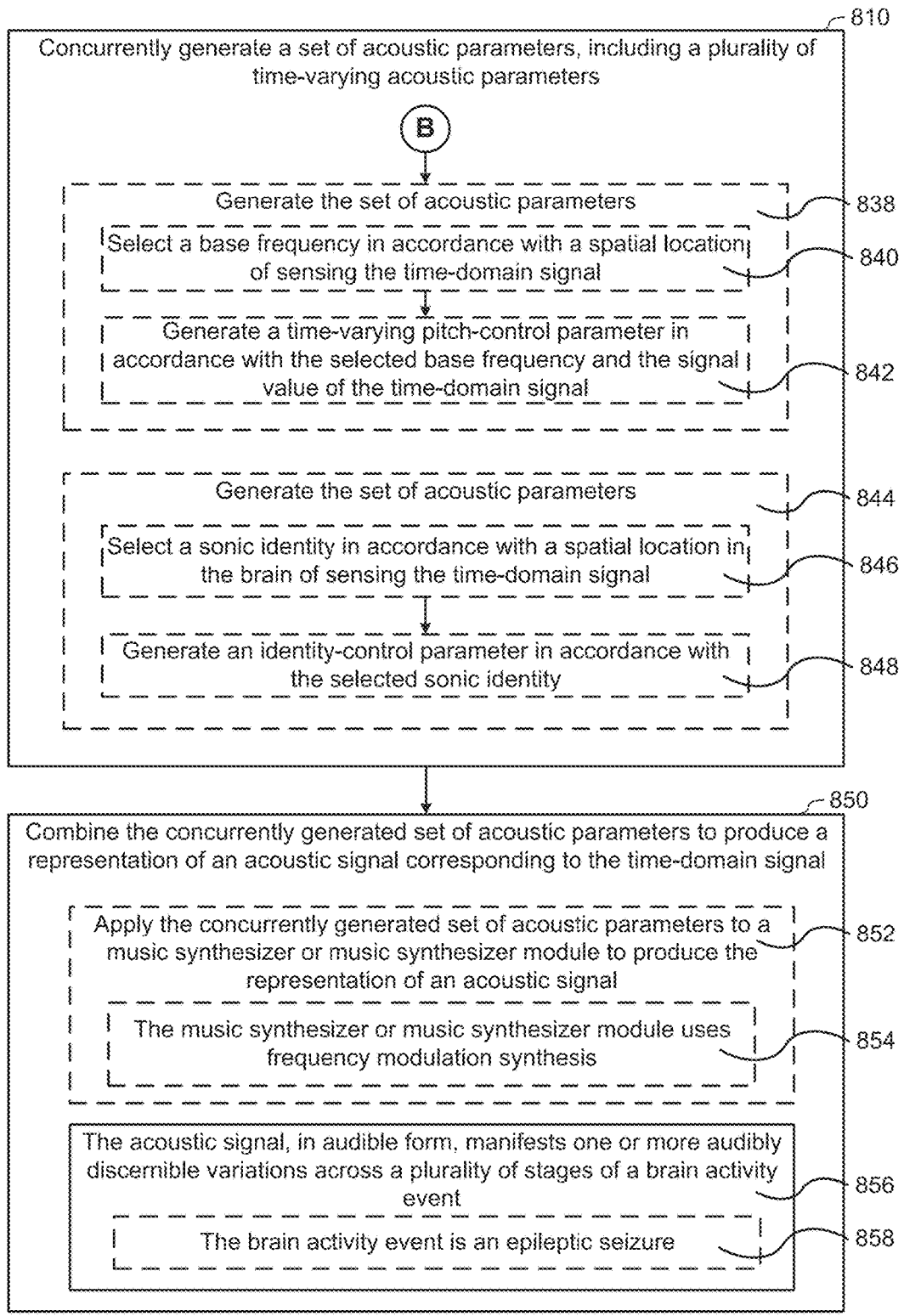

FIGS. 8A-8C is a flowchart representing process 800 for sonifying electrical activity (e.g., electrical signals) obtained from a subject, according to certain embodiments of the invention. In some embodiments, process 800 is performed at a handheld or wearable device (e.g., device 900, FIGS. 9A-9C, device 1000, FIGS. 10A-10B, and/or device 1100, FIG. 11, device 100, FIGS. 1A-16). Process 800 is optionally governed by instructions that are stored in a computer readable storage medium and that are executed by a digital processor system (or, optionally, one or more digital processor systems) (e.g., digital processor system 560, which in various embodiments is or is a component of any of the aforementioned handheld or wearable devices). Each of the operations shown in FIGS. 8A-8C optionally corresponds to instructions stored in a computer memory or computer readable storage medium. The computer readable storage medium optionally includes a magnetic or optical disk storage device, solid state storage devices such as flash memory, or other non-volatile memory device or devices. The computer readable instructions stored on the computer readable storage medium are in source code, assembly language code, object code, or another instruction format that is interpreted by one or more processors. Moreover, elements and/or operations of process 800 can be combined in separately, in combination, or as a whole with any operations recited as a part of process 300 in several embodiments of the invention.

For ease of explanation, process 800 is described with reference to brain activity (e.g., process 800 is described as a method for sonifying one or more electrical signals obtained from a subject's brain). In some embodiments, however, process 800 is used to sonify signals representing other bodily functions (e.g., electrocardiography (EEG) signals).

The digital processor system obtains (802) a time-domain signal (e.g., time-domain signal 618, FIG. 6B) representing brain activity, the time-domain signal having a time-varying signal value. In some embodiments, the time-domain signal representing brain activity is obtained (804) from one or more electrodes. For example, as explained with reference to FIG. 5 and FIG. 6B, time-domain signal 618 (FIG. 6B) is obtained from sensors 510 located at particular locations on the subject's head. The sensors 510 include one or more electrodes. In some embodiments, the device is a wearable device (FIG. 11) and sensors 510 are substantially fixed at their particular locations. In some implementations, the device is a handheld device (FIGS. 9A-9C, FIGS. 10A-10B) and the sensors are placed by the subject, or by someone else, at their respective locations. In some implementations, differential voltages (e.g., differences in voltage values) are measured between two measurement locations (e.g., between two electrodes) to produce a differential voltage signal (e.g., a bipolar voltage signal) corresponding optionally to sensor time-domain signal 601 (FIG. 6A) or to time-domain signal 618 (FIG. 6B).

The time-domain signal representing brain activity is obtained by conditioning (806) a sensor time-domain signal obtained from the one or more electrodes. For example, as shown in FIG. 5 and FIGS. 6A-2B, sensor time-domain signal 601 is obtained from a sensor 510 and—after optionally being pre-processed by analog front end 520 to produce filtered sensor time-domain signal 607—is conditioned by signal conditioning module 530.

In some embodiments, the conditioning includes (808) up-sampling the sensor time-domain signal to produce a first intermediate signal and low pass filtering the first intermediate signal to produce the time-domain signal representing brain activity or a signal corresponding to the time-domain signal representing brain activity. For example, as shown in FIG. 6B, filtered sensor time-domain signal 607—after conversion from an analog signal to a corresponding digital signal—is up-sampled (e.g., by up-sampler 612, FIG. 6B) to produce a first intermediate signal (e.g., first intermediate signal 614, FIG. 6B). For example, as explained above, if the original sampling rate of the digital representation of the analog filtered sensor time-domain signal corresponds to 500 Hz, the first intermediate signal (e.g., first intermediate signal 614) produced by up-sampler 612 has a sampling rate used in conventional audio applications (e.g., 48 kHz). First intermediate signal 614 is then low pass filtered (e.g., by digital low pass filter 616, FIG. 6B) to produce the time-domain signal representing brain activity or a signal corresponding to the time-domain signal representing brain activity (e.g., time-domain signal 618, FIG. 6B).

The digital processor system concurrently generates (810) a set of acoustic parameters (e.g., see operations 812-848), including a plurality of time-varying acoustic parameters. In this context, parameters are "concurrently generated" even if they are literally generated serially by single-threaded processor, when the resulting parameters are used or applied concurrently for generating an audio signal, or a representation of an audio signal. Typically, two or more concurrently generated parameters are generated or updated in response to a stream of digital signal values corresponding to the time-domain signal.

One or more of the plurality of time-varying acoustic parameters is modulated (812) in accordance with at least the signal value of the time-domain signal. For example, as explained above with reference to FIG. 6C, signal modulator 540 (optionally included in digital processor system 560) concurrently generates a set of acoustic parameters, including a plurality of time-varying acoustic parameters. In some embodiments, as described in relation to FIG. 6C above, the plurality of acoustic parameters includes a vibrato or frequency-control parameter (e.g., frequency-control parameter 622-*a*), a vowel-control parameter (e.g., vowel-control parameter 622-*b*), and/or a time-varying amplitude or intensity-control parameter (e.g., intensity-control parameter 622-*c*). In some embodiments, the set of acoustic parameters includes a pitch-control parameter (e.g., pitch-control parameter 622-*d*) and/or a sonic identity parameter (e.g., sonic identity parameter 622-*e*).

In some embodiments, generating a plurality of acoustic parameters includes (814) generating a vibrato or frequency-control parameter (as described herein with respect to operations 816-820). For example, as described above with reference to FIG. 6C, signal modulator 540 (optionally included in a digital processor system) includes vibrato modulator 620-*a*, which generates frequency-control parameter 622-*a*.

In some embodiments, the digital processor system obtains (816) a base frequency. In some embodiments, the digital processor system modulates (818) the base frequency in accordance with the signal value of the time-domain signal, to produce a signal-dependent variation of the base frequency. In some embodiments, the digital processor system generates (820) a frequency-control parameter corresponding to the signal-dependent variation of the base frequency. For example, as explained above, vibrato modulator (e.g., vibrato modulator 620-*a*, FIG. 6C) generates a control parameter for controlling the amount of vibrato (which can be considered to be the amount of frequency variation) produced by a music or audio synthesizer. In some implementations (e.g., implementations in which pitch and vibrato are controlled during audio synthesis by separate parameters) the frequency-control parameter is independent of the base frequency or pitch, while in other implementations the frequency-control parameter incorporates the base frequency or pitch.

In some embodiments, generating a plurality of acoustic parameters includes (822) generating a vowel-control parameter (as described herein with respect to operations 824-830). For example, as shown in FIG. 6C, signal modulator 540 (optionally included in digital processor 560) comprises vowel modulator 620-*b* which generates vowel-control parameter 622-*b*.

In some embodiments, a digital processor (e.g., digital processor 560) sequentially selects (824) acoustic waveform patterns from a ordered set of N acoustic waveform patterns, the set of N acoustic waveform patterns arranged in a predefined order, where N is an integer greater than 2. In some embodiments, the sequence of selected acoustic waveform patterns includes (826) a sequence of vowel waveform patterns. In some embodiments, a digital processor (e.g., digital processor 560) modulates (828) a rate of sequentially selecting acoustic waveform patterns in accordance with the signal value of the time-domain signal, to produce a signal-dependent rate of variation of acoustic waveform patterns. In some embodiments, a digital processor (e.g., digital processor 560) generates (830) a vowel-control parameter corresponding to the signal-dependent rate of variation of acoustic waveform patterns.

For example, as described above, vowel modulator (e.g., vowel-control parameter 622-*b*) modulates a rate of sequentially selecting acoustic waveform patterns from a set of 12 acoustic waveform patterns in accordance with the signal value of the time-domain signal (e.g., time-domain signal 618, FIG. 6C). For example, for an increase in signal value of the time-domain signal (e.g., time-domain signal 618), vowel modulator (e.g., vowel-control parameter 622-*b*) selects (e.g., scans through) a sequence of acoustic waveform patterns from a set of 12 acoustic waveform patterns more rapidly or at an increased rate; conversely, for a decrease in signal value of the time-domain signal (e.g., time-domain signal 618), vowel modulator (e.g., vowel-control parameter 622-*b*) selects (e.g., scans through) a sequence of acoustic waveform patterns from a set of 12 acoustic waveform patterns more gradually (e.g., slowly) or at a decreased rate.

In some embodiments, the digital processor system generates (832) a plurality of acoustic parameters, as described herein with respect to operations 834-836. In some embodiments, the digital processor system computes (834) a time-varying amplitude value in accordance with the signal value of the time-domain signal. In some embodiments, the digital processor system generates (836) a time-varying intensity-control parameter corresponding to the computed time-varying amplitude value.

For example, as described above in relation to FIG. 6C, an intensity modulator (e.g., intensity modulator 620-*c*, FIG. 6C) computes a time-varying amplitude value in accordance with the signal value of the time-domain signal (e.g., time-domain signal 618, FIG. 6C) and generates a time-varying intensity-control parameter (e.g., intensity-control parameter 622-*c*, FIG. 6C) corresponding to the computed time-varying amplitude value. In some implementations, for an increase in signal value of the time-domain signal (e.g., time-domain signal 618), the time-varying amplitude value—and corresponding time-varying intensity-control parameter (e.g., intensity-control parameter 622-*c*)—computed by intensity modulator (e.g., intensity modulator 620-*c*) increases. Conversely, for a decrease in signal value of the time-domain signal (e.g., time-domain signal 618), the time-varying amplitude value—and corresponding time-varying intensity-control parameter (e.g., intensity-control parameter 622-*c*)—computed by intensity modulator (e.g., intensity modulator 620-*c*) decreases.

In some embodiments, the digital processor system generates (838) the set of acoustic parameters, as described herein with respect to operations 840-842. In some embodiments, the digital processor system selects (840) a base frequency in accordance with a spatial location of sensing the time-domain signal. In some embodiments, the digital processor system generates (842) a time-varying pitch-control parameter in accordance with the signal value of the time-domain signal, and optionally in accordance with the selected base frequency. For example, as shown in FIG. 6C, signal modulators 540 (optionally included in digital processor 560) comprises pitch modulator 620-*d* which generates pitch-control parameter 622-*d* in accordance with a signal value of the time-domain signal (e.g., time-domain signal 618), and optionally in accordance with a selected base frequency (e.g., corresponding to a spatial location of sensing the time-domain signal).

Without limitation with respect to other implementations, in some implementations the set of acoustic parameters are generated, in accordance with a set of instructions executed by one or more processors of a digital processor system, as described above. The following is an example of a pseudo-code representation of instructions for generating the set of acoustic parameters, once per time period (e.g., once every 10 milliseconds), where SigVal is the signal value for the current time period:

// amplitude
    amplitude.param=max(0.0, c1+c2*SigVal);
    //pitch
    pitch.param=ConvertMidiToFreq(c3−c4*SigVal),
    // vibrato
    vibrato-gain.param=pitch.param*($2^{c5}$−1);
    vibrato.param=vibrato.param+c6*SigVal;
    vibrato.freq.param=max(0.0, min(c7, c8+vibrato.param));
    //vowel
    vow=vow+(c9*SigVal);
    vowel.param=integer (abs(vow)) modulo 12;

where, in one example, the following coefficient values are used: c1=0.1, c2=20, c3=45, c4=5, c5=0.05, c6=4, c7=8.0, c8=4.5, c9=20. Further, "ConvertMidiToFreq" is a function for converting a midi note to a frequency value, "max" is a function that outputs the maximum of its input values, "min" is a function that outputs the minimum of its input values, "abs" is a function that outputs the absolute value of its input, and "integer" is a function that outputs the integer portion of its input. In another example, in which two or more multiple time-domain signals are processed to produce a corresponding number of audio signals (sometimes called voices for ease of reference), one or more of the coefficients (e.g., c1 to c9 in the above example) are different for different ones of the audio signals, thereby producing audio signals that are audibly distinct. In one example, coefficients c3 (corresponding to base frequency) and c6 (corresponding to amount of vibrato) and c9 (corresponding to a rate at which the audio signal traverses a sequence of vowels or phonemes), have different values for each audio signal.

For example, as shown in FIG. 5, sensors 510 are located at different spatial locations in the brain for sensing the time-domain signal (e.g., sensor time-domain signal 601), and a base frequency (e.g., a pitch) is selected in accordance with a spatial location in the brain of sensing the time-domain signal. In this example, for a time-domain signal obtained from the left hemisphere in the brain, a lower base frequency (e.g., a frequency corresponding to the pitch of a baritone voice) is selected; whereas for a time-domain signal obtained from the right hemisphere in the brain, a higher base frequency (e.g., a frequency corresponding to the pitch of a tenor voice) is selected.

In some embodiments, the digital processor system generates (844) the set of acoustic parameters, as described with respect to operations 846-848. In some embodiments, the digital processor system selects (846) a sonic identity in accordance with a spatial location in the brain (or, alternatively, on the surface of the cranium) of sensing the time-domain signal. In some embodiments, the digital processor system generates (848) an identity-control parameter in accordance with the selected sonic identity. For example, as shown in FIG. 6C, signal modulator 540 (optionally included in digital processor 560) comprises sonic identity modulator 620-*e* which generates sonic identity parameters 622-*e* in accordance with a selected sonic identity corresponding to a spatial location in the brain of sensing the time-domain signal. As a more specific example, in some embodiments, device 900 (FIGS. 9A-9C), device 1000 (FIGS. 10A-10B), or device 100 (FIGS. 1A-1B) automatically detect whether the signal produced by the plurality of electrodes represents a heartbeat signal or a brain signal and selects a sonic identity accordingly.

For example, as shown in FIG. 5, sensors 510 are located at different spatial locations in the brain for sensing the time-domain signal (e.g., sensor time-domain signal 601), and a sonic identity is selected in accordance with a spatial location in the brain (or, alternatively, on the surface of the cranium) of sensing the time-domain signal. As a more specific example, in some embodiments, device 1100 selects distinct sonic identities for the left brain (e.g., produced by a voltage difference between sensors 510-4 and 510-5) and the right brain (e.g., produced by a voltage difference between sensors 510-6 and 510-7). In this example, for a time-domain signal obtained from the left hemisphere in the brain, a sonic identity is selected corresponding to the sonic identity of (e.g., acoustic characteristics defining or associated with) a violin (or a first "voice"); whereas for a time-domain signal obtained from the right hemisphere in the brain, a sonic identity is selected corresponding to the sonic identity of (e.g., acoustic characteristics defining or associated with) a guitar (or as second "voice"). In some implementations, the sonic identity is simply the base frequency of each generated acoustic signal (or representation of an acoustic signal), while in some other implementations, the sonic identity determines both the base frequency and one or more parameters (e.g., multipliers, offsets, etc.) that are used while generating the acoustic parameters corresponding to each time-domain signal (e.g., corresponding to each sensor signal being sonified).

The digital processor system combines (850) the concurrently generated set of acoustic parameters to produce a representation of an acoustic signal corresponding to the time-domain signal. For example, as shown in FIG. 6C, synthesizer module 550 (optionally included in digital processor 560) combines the concurrently generated set of acoustic parameters generated by signal modulator 540 to produce a representation of an acoustic signal (representation of acoustic signal 630) corresponding to the time-domain signal (e.g., time-domain signal 618).

In some embodiments, the digital processor system applies (852) the concurrently generated set of acoustic parameters to a music synthesizer or music synthesizer module to produce the representation of an acoustic signal. In some embodiments, the music synthesizer or music synthesizer module uses (854) frequency modulation synthesis. For example, as shown in FIG. 6C, synthesizer module 550 uses frequency modulation synthesis implemented on frequency modulation synthesizer 624.

In some circumstances, the acoustic signal, in audible form, manifests (856) one or more audibly discernible variations across a plurality of stages of a brain activity event. In some embodiments, the brain activity event is (858) an epileptic seizure, or other event corresponding to abnormal brain activity. For example, the acoustic signal corresponding to representation of acoustic signal 630, in audible form, manifests one or more audibly discernible variations (e.g., variations in vibrato, in rate of change of vowel, and/or in intensity) across a plurality of stages of a brain activity event. In some embodiments in which the brain activity event is an epileptic seizure, the acoustic signal in audible form manifests one or more audibly discernible variations (change in volume, pitch, rate of vowel change) across the stages (e.g., normal state, pre-ictal phase, seizure phase and postictal phase) of the epileptic seizure. For example, the acoustic signal is periodic and has higher amplitude during the seizure phase, and is chaotic (has lower or little periodicity) and has lower amplitude during the normal state.

In some implementations, the brain activity event for which brain electrical signals are sonified is not an epileptic seizure, and instead is a respective brain activity event that is the subject of analysis or monitoring. For example, in some implementations the brain activity event for which brain electrical signals are sonified comprises brain activity while the human subject performs various tasks (e.g., mental tasks, physical tasks, operating an apparatus, answering questions, playing a musical instrument, taking an exam, performing or attempting to perform multiple tasks or functions concurrently, etc.), brain activity associated with experiencing various external stimuli, brain activity associated with physiological functions, brain activity associated with various diseases, and the like.

E. Signal Reception Devices

Figure 9A:
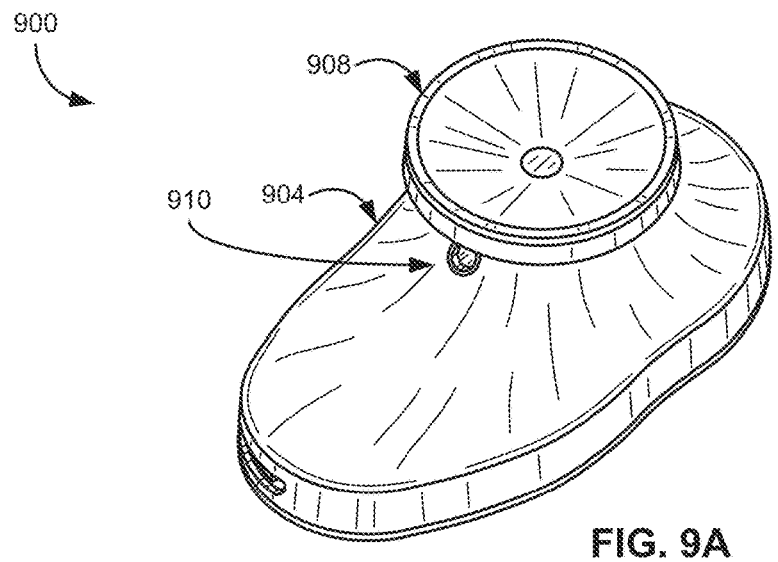
FIGS. 9A-9C are illustrations from a variety of perspectives of a handheld device for sonifying electrical signals obtained from a subject, in accordance with some embodiments of the invention.
Figure 9B:
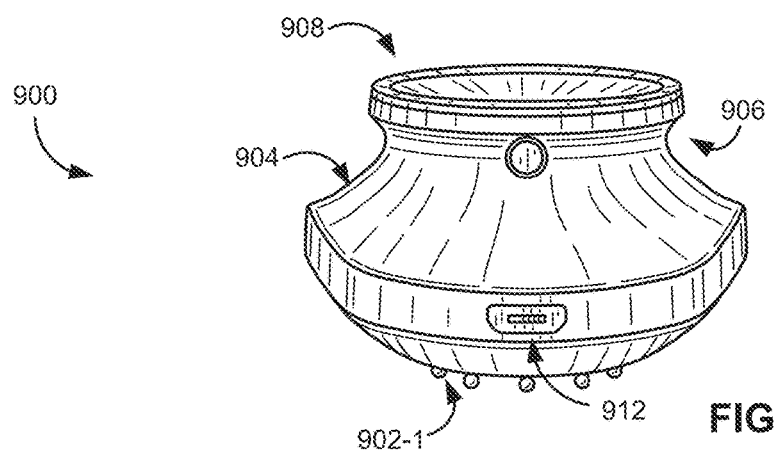
Figure 9C:
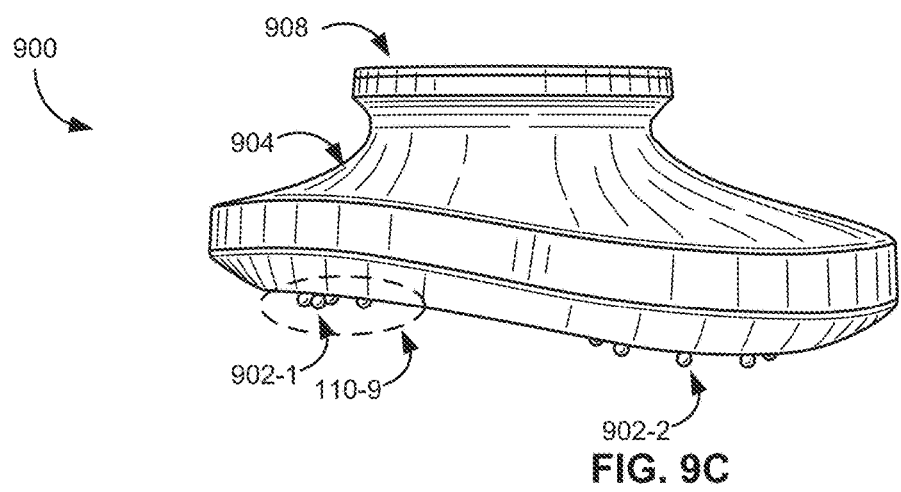

FIGS. 9A-9C are illustrations from a variety of perspectives of a handheld device 900 for sonifying electrical signals (e.g., time-domain electrical signals) obtained from a subject, in accordance with some embodiments. In some implementations, device 900 is configured to be a "pocket-sized" handheld device (e.g., sized to fit in the pocket of a physician's typical lab coat).

In various embodiments, device 900 may share any of the features described with reference to device 1000 (FIGS. 10A-10B), device 1100 (FIG. 11), and/or device 100 (FIG. 5A-1B), unless context makes clear that such features are incompatible with device 900. Likewise, device 1000, device 1100, and/or device 100 may share any of the features described with reference to device 900 unless context makes clear that such features are incompatible with a respective one of those devices.

In some implementations, device 900 includes a plurality of electrodes 902 (e.g., electrode 902-1 and electrode 902-2). In some embodiments, electrodes 902 are dry electrodes, while in other embodiments, electrodes 902 are wet electrodes. In some embodiments, various components of device 900 are incorporated into housing 904. In some embodiments, electrodes 902 are rigidly coupled with housing 904 (e.g., the plurality of electrodes includes dry or wet electrodes, at least a portion of which extend or protrude from (e.g., outside of) housing 904 of device 900). In some other embodiments, electrodes 902 are inserted in or held by a headband and coupled with circuitry in housing 904 via one or more electrical connectors.

In some embodiments, housing 904 includes handle 906. For example, handle 906 of device 900 is used to apply the device to the subject in a manner similar to how a physician would apply a stethoscope to a patient (e.g., handle 906 is gripped between the user's thumb and index finger). Thus, in some embodiments, device 900 is small enough to be comfortably held between a user's thumb and index finger.

In some embodiments, housing 904 fits within a cube with dimensions of 10 centimeters (cm) by 7 centimeters by 7 centimeters. In some embodiments, housing 904 fits within a cube with dimensions of 7 centimeters (cm) by 5 centimeters by 5 centimeters. In some embodiments, housing 904 fits within a cube with dimensions 6 centimeters (cm) by 4 centimeters by 4 centimeters. In some embodiments, housing 904 fits within a sphere having a radius of 3 centimeters (cm).

Electrodes 902 are configured to be placed at respective locations on the subject's body. For example, in some embodiments, the electrodes of the plurality of electrodes 902 are configured to be placed at respective locations on the subject's head. The plurality of electrodes includes a first electrode 902-1 that is configured to be placed at any of a plurality of locations on the subject's head. That is to say, the first electrode is capable of being moved (e.g., intended to be moved) to different locations on the subject's head. As shown in the present example, device 900 is itself intended to be placed at any of a plurality of locations on the subject's head. For example, a physician (or the subject herself) might place device 900 on the left side of the subject's head to "listen" to brain activity in the left hemisphere of the subject's brain, then subsequently place device 900 on the right side of the subject's head to "listen" to brain activity in the right hemisphere of the subject's head. Thus, in some embodiments, device 900 allows the user to perform a bilateral aural comparison of the subject's brain activity.

In some embodiments, multiple electrodes are attached to the subject's head using a headband or adhesive and coupled with housing 904 via one or more electrical connectors. For example, a first set of electrical connectors may connect a first set of electrodes positioned near the subject's left hemisphere to circuitry in housing 904, and a second set of electrical connectors may connect a second set of electrodes positioned near the subject's right hemisphere to circuitry in housing 904. Using such embodiments, a physician (or the subject herself) can listen to brain activity in the left hemisphere of the subject and brain activity in the right hemisphere of the subject.

In some embodiments, the plurality of electrodes 902 is grouped into sensors 510 (e.g., first electrode 902-1 is grouped into sensor 510-9 with several other electrodes, which have not been labeled for visual clarity). In some embodiments, sensors 510 include only a single electrode. In some embodiments, sensors 510 each includes two or more electrodes that are electrically (e.g., conductively) coupled (e.g., the two or more electrodes within a respective sensor 510 provide a better electrical contact with the subject's skin). The plurality of electrodes produces one or more electrical signals corresponding to brain activity. In some embodiments, the one or more electrical signals are bipolar (e.g., differential) signals representing a voltage difference between two of the electrodes (e.g., electrode 902-1 and electrode 902-2).

Device 900 includes an analog-to-digital (A/D) converter (e.g., analog-to-digital converter 608, FIG. 6B) to digitize the one or more electrical signals and a processor (e.g., digital processor system 560, FIG. 1A-1B, FIGS. 7A-3B) that receives the one or more digitized electrical signals and produces a representation of an acoustic signal (e.g., representation of acoustic signal 630, FIG. 6C). In some embodiments, the analog-to-digital (ND) converter and the processor are contained within housing 906. In some embodiments, device 900 includes an accelerometer (e.g., accelerometer 784, FIG. 7A) within its housing. Signals from the accelerometer indicating mechanical movement of the subject can be used to initiate removal of artifacts in the electrical signals that are due to mechanical movement of the subject (e.g., as described with reference to process 300, FIG. 3). In some embodiments, device 900 is programmed to apply a low-pass filter to remove artifacts in the electrical signals that are due to muscle convulsions (e.g., as described with reference to process 300, FIG. 3). In some embodiments, device 900 includes an affordance (e.g., a physical or touch screen button) to turn on/off the low-pass filter.

Device 900 includes speaker system 908 that sonifies the representation of the acoustic signal. In some embodiments, speaker system 908 is positioned within housing 904. Alternatively, or in addition to speaker system 908, in some embodiments, device 900 includes a first output port through which to attach headphones. In some implementations, not shown, speaker system 908 is embodied as headphones/ear pieces (e.g., in a manner similar to conventional stethoscopes).

In some embodiments, the one or more electrical signals represent electroencephalography (EEG) data that are concordant with laboratory EEG data, such as laboratory EEG data obtained from one or more human test subjects. In some embodiments, the handheld device is sufficiently sensitive that it produces verified EEG data (e.g., rather than muscle tone data and/or a mixture of EEG and muscle tone data). In some embodiments, the laboratory EEG data is obtained from electrodes surgically implanted into one or more human test subjects' brains to verify that the handheld device produces EEG data that are concordant with what would be obtained in a laboratory setting.

In some embodiments, the processor (e.g., digital processor system 560, FIGS. 7A-7B) is configured to produce a feedback signal indicating whether the one or more electrical signals represent electroencephalography (EEG) data that are concordant with laboratory EEG data. In some embodiments, the processor calculates a quality-metric corresponding to data received in the one or more electrical signals and compares the quality-metric to a threshold to determine if the one or more electrical signals represent EEG data that are concordant with laboratory EEG data. For example, in some embodiments, the quality-metric is an estimate of the amount of the electrical signals attributable to EEG data compared with non-EEG sources (such as muscle-tone signals and/or noise) (e.g., an EEG to non-EEG ratio estimate). In some embodiments, a predetermined threshold is selected to provide a desired confidence level that the EEG data are concordant with the laboratory EEG data, which are obtained as described above. Thus, when the EEG to non-EEG ratio estimate exceeds the predetermined threshold, the processor determines that the one or more electrical signals representing EEG data are concordant with laboratory EEG data and produces a corresponding feedback signal. In some embodiments, device 900 includes a light-emitting diode (LED) that the processor turns on when the processor determines that the one or more electrical signals representing EEG data are concordant with laboratory EEG data (e.g., the LED lights up). Alternatively, or in addition to the LED, in some embodiments, the feedback signal is presented to the user as an aural and/or tactile feedback signal.

For example, in some embodiments the device is configured to produce a first sound and/or first tactile feedback when it is receiving electrical signals that are not concordant with laboratory EEG data. The user thereby knows to change the position of the device's electrodes until the first sound and/or first tactile feedback stops being produced. Alternatively, in some embodiments, the device is configured to suppress the generation of a representation of an acoustic signal and/or the sonification of the acoustic signal until the received electrical signals are determined by the device to be concordant with laboratory EEG data. In such embodiments, the user thereby knows to change the position of the device's electrodes until the device produces "brain activity sonification" sounds, and furthermore the user can have a high degree of confidence that the sounds produced are in fact a sonification of the subject's EEG signals.

In some embodiments, device 900 includes memory (e.g., memory 710, FIG. 7A) that stores electroencephalography (EEG) data corresponding to the one or more electrical signals obtained from the subject. In some embodiments, the EEG data is stored in the form of audio data (e.g., audio data that represents the generated acoustic signal is stored as an audio file, such as a WAV file or MP3 file). In some embodiments, the EEG data is stored as raw EEG data. In some embodiments, the EEG data is stored remotely (e.g., on the "cloud"). For example, in some embodiments, device 900 integrates with a mobile application on a smart-phone via a wireless connection (e.g., a Bluetooth connection). Device 900 transmits EEG data (e.g., raw data and/or audio data) using the wireless connection to the smart-phone, which transmits the raw data to a remote server (e.g., a Cloud server) using a mobile network (e.g., a 4G Network). In some circumstances, the EEG data on the remote server is made available to a physician for review. In some embodiments, device 900 is operable with a mobile network to communicate with the remote server. In some embodiments, device 900 includes a wired output port 912 (e.g., a USB port, micro-USB port, or the like) for connection with an external computer (e.g., a desktop/laptop computer, smart-phone, etc.). In some embodiments, the EEG data is downloadable to the external computer through the output port 912.

In some embodiments, device 900 includes a voice recorder that stores voice data in the device's memory (e.g., data storage 570 of memory 710, FIG. 7A). In some embodiments, the voice recorder includes a microphone 910. In some circumstances, the voice recorder records voice data (e.g., the user's voice) for a predetermined amount of time (e.g., 9-10 seconds) before (or concurrently with) acquiring EEG data. During this time, the user can verbally document the procedures being followed. For example, before taking EEG data on the left side of the subject's head, the user (who may be the subject) will say "I am now applying the device to the left side of the patient's head." In some embodiments, the device provides spoken (i.e., audible) instructions to the user (e.g., using speaker 908), saying, for example, "Please apply the device to the left side of the patients head." The voice recorder is then used to document confirmation that the instructions are being followed (again, by having the user say, "Ok, I'm now applying the device to the left side of the patient's head"). In some embodiments, the voice data is time-stamped.

In some embodiments, application of an electrode of the plurality of electrodes to, respectively, the left and right halves of the human subject's head yields audible indicia of the presence or absence of stroke. For example, in some embodiments, a stroke effecting the right (or left) side of the subject's head is indicated when the right (or left) side of the subject's head yields a substantially quieter sonified acoustic signal than the left (or right) side of the subject's head.

In some embodiments, the sonified representations of the acoustic signal include audible indicia of the presence or absence of seizure (e.g., indicated by rhythmic beating in the sonified acoustic signal), a postictal state, central nervous system depression, concussion, normal brain function, or brain death (e.g., indicated by total or near total quiet in the sonified acoustic signal).

Figures 10A, 10B:
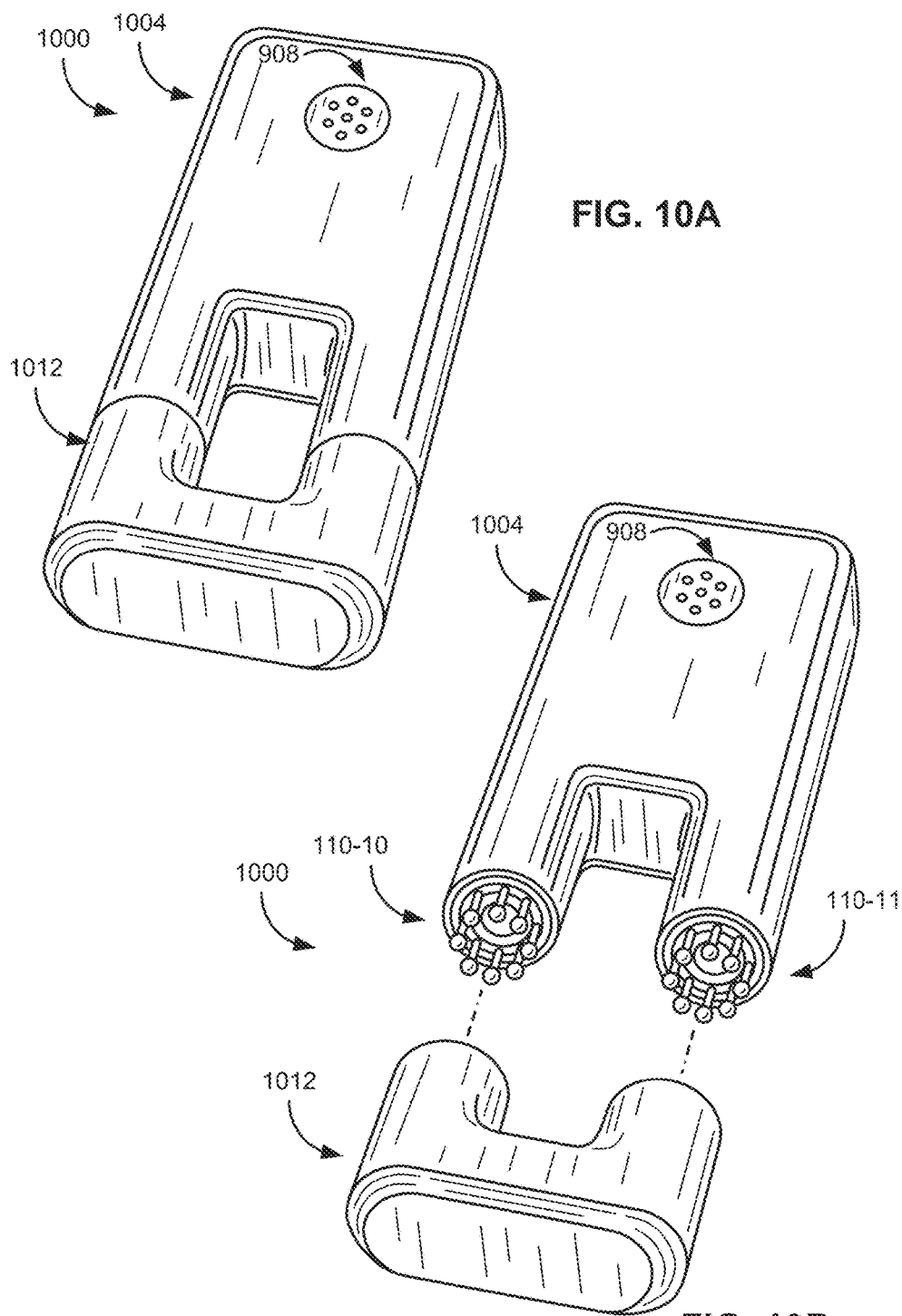
FIGS. 10A-10B are illustrations of another handheld device for sonifying electrical signals obtained from a subject, in accordance with some embodiments of the invention.
Figure 11:
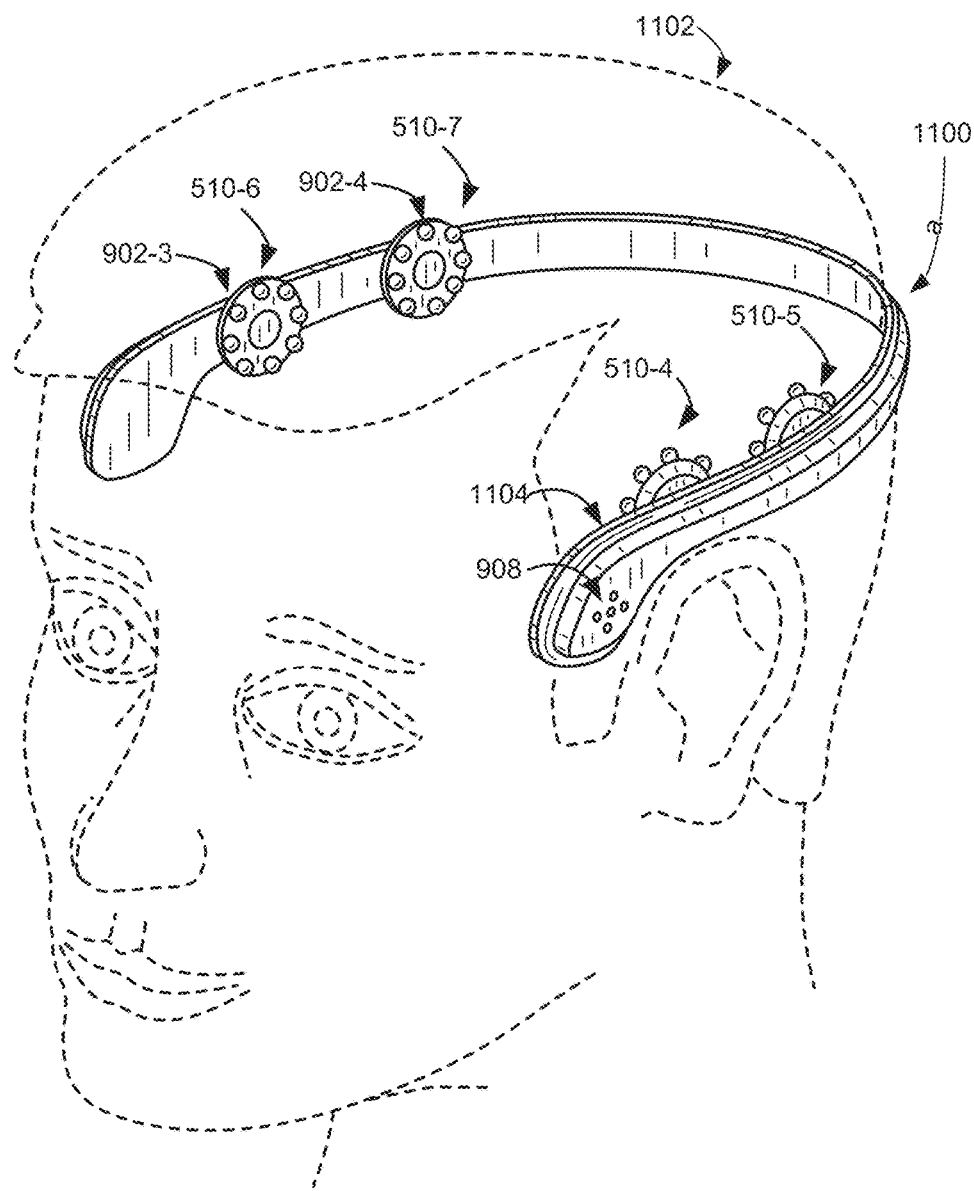
FIG. 11 is an illustration of a wearable device for sonifying electrical signals obtained from a subject, in accordance with some embodiments of the invention.

FIGS. 10A-10B are illustrations of another handheld device 1000 for sonifying electrical signals obtained from a subject, in accordance with some embodiments. In various embodiments, device 1000 may share any of the features described with reference to device 900 (FIGS. 9A-9C), device 1100 (FIG. 11), and/or device 100 (FIG. 1A-1B), unless context makes clear that such features are incompatible with device 1000. Likewise, device 900, device 1100, and/or device 100 may share any of the features described with reference to device 1000 unless context makes clear that such features are incompatible with a respective one of those devices.

Device 1000 is configured to be a "pocket" handheld device. To that end, device 1000 includes a housing 1004 that is shaped to more naturally fit within a user's pocket. In some embodiments, housing 1004 fits within a cube with dimensions of 10 centimeters (cm) by 7 centimeters by 3 centimeters. In some embodiments, housing 1004 fits within a cube with dimensions of 7 centimeters (cm) by 7 centimeters by 3 centimeters. In some embodiments, housing 1004 fits within a cube with dimensions of 12 centimeters (cm) by 6 centimeters by 3 centimeters. In addition, device 1000 includes a cap 1012 to cover sensors 510-10 and 510-11 to protect sensors 510 while device 1000 is in the user's pocket.

It should be noted that electrodes 902 are not necessarily incorporated into the devices described herein. In particular, as an alternative to the embodiments shown in FIGS. 9A-9C and FIGS. 10A-10B, in which the electrodes are incorporated (at least partially) and/or rigidly coupled with the housing of the device, in some embodiments, the device includes an input port configured to couple a plurality of electrodes to the device and to receive one or more electrical signals produced by the plurality of electrodes. For example, in some embodiments, the electrodes are disposable (e.g., similar to commercially available ECG or EEG electrodes). In some embodiments, the electrodes are tethered to device through an input port. In some embodiments, the devices described herein include a plurality of electrodes (e.g., device 900 and/or device 1000) and also include an input port through which to tether additional electrodes. In some embodiments, the device is wearable on the user's wrist (e.g., the device is a smart watch) and is configured to be tethered to electrodes that are placed over the user's fingers. In such embodiments, the user can sonify brain signals by touching the subject's head.

FIG. 11 is an illustration of a wearable device 1100 for sonifying electrical signals obtained from subject 1102, in accordance with some embodiments. In various embodiments, device 1100 may share any of the features described with reference to device 900 (FIGS. 9A-9C), device 1000 (FIGS. 10A-10B), and/or device 100 (FIG. 1A-1B), unless context makes clear that such features are incompatible with device 1100. Likewise, device 900, device 1000, and/or device 100 may share any of the features described with reference to device 1100 unless context makes clear that such features are incompatible with a respective one of those devices.

Device 1100 includes a plurality of electrodes 902. As mentioned above, these electrodes can be dry or wet electrodes. Electrodes 902 are configured to be placed at respective locations on the subject's head. For example, in some embodiments, electrode 902-3 and electrode 902-4 are positioned (placed) substantially at predefined locations when subject 1102 wears device 1100. The plurality of electrodes produces one or more electrical signals corresponding to brain activity. For example, device 1100 includes sensors 510-4 and 510-5 which produce an electrical signal corresponding to left hemisphere brain activity, and further includes sensors 510-6 and 510-7 which produce an electrical signal corresponding to right hemisphere brain activity. Device 1100 includes an analog-to-digital (ND) converter to digitize the one or more electrical signals and a processor that receives the one or more digitized electrical signals and produces a representation of an acoustic signal. Device 1100 further includes a speaker system 908 that sonifies the representation of the acoustic signal. In some embodiments, the A/D converter, the processor, and the speaker system are incorporated into wearable housing 1104. In some embodiments, wearable housing 1104 is a headband, a helmet, or a hat. In some embodiments, wearable housing 1104 includes a headband that includes an adjustable strap or housing that is configured to fully wrap around the subject's head to stably hold the wearable housing on the subject's head. In some embodiments, device 1100 interfaces with a chest strap having one or more electrodes to measure a heartbeat signal concurrently with the brain signals.

Device 1100 is used in some circumstances for long-term monitoring of rarely (e.g., sparsely or infrequently) occurring conditions. For example, in some embodiments, device 1100 is used to produce diagnostics for neurology patients complaining of an altered mental state, such as dizziness, lightheadedness, or vertigo. To that end, device 1100 can be worn for prolonged periods of time without becoming awkward or uncomfortable. In addition, device 1100 can be easily removed for bathing and the like. This convenience allows device 1100 to monitor a patient for a month or longer, greatly increasing the likelihood that an episode will be measured by device 1100 and thus produce EEG data of an episode that is available for a neurologist to review. As another example, in some circumstances, device 1100 is worn by epileptics and/or patients with other types of diagnosed conditions to alert them of an on-coming episode. For example, an epileptic patient will wear device 1100 while driving. Device 1100 continuously monitors the epileptic patient for indicia of a pre-ictal state, which signifies that the patient is likely to start seizing. When the device detects indicia of an ictal state, the device alerts the patient using speaker 908, stating, e.g., "Pull Over! Pull Over! Seizure detected!"

F. Preliminary Results Using Sonification Devices

Figure 12:
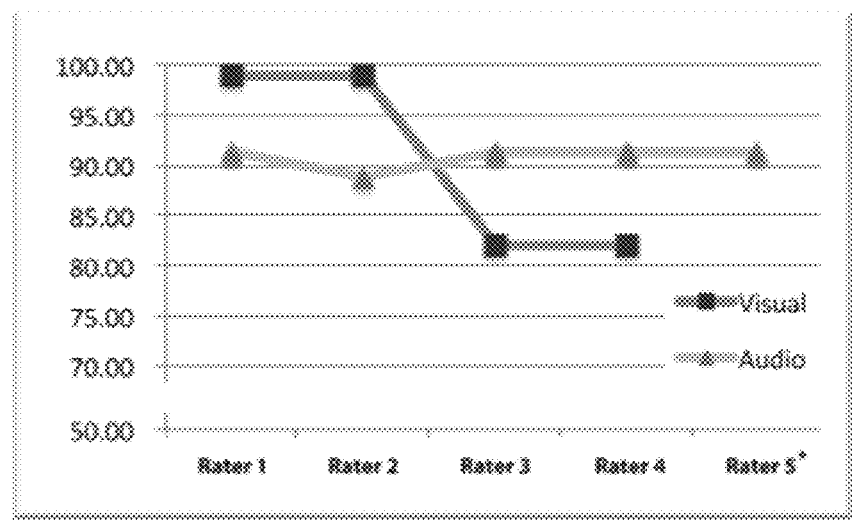
FIG. 12 provides several tables showing experimental results in accordance with some embodiments of the invention.

The following discussion involves experimental results in accordance with several embodiments of the invention shown in the tables in FIG. 12. For instance, a seizure can be reliably detected by the sound of it when sonified by sonification device in accordance with many embodiments of the invention. In 4 independent surveys shown in table 1201 in FIG. 12, including clinicians and non physicians (even high school students), >200 participants listened to 8 samples of sonified EEG data from sonification of several embodiments during normal (n=4) or seizure activity (n=4) recorded from real ICU cases. As shown in table 1201, the results showed little differences between the prediction power of physicians and non-physicians.

Moreover, as shown in table 1205 sonified EEG is comparable to Visual EEG in distinguishing seizures. A 15-second-long visual display of EEGs (recorded with conventional EEG system) from 56 ED and ICU recordings at Stanford Medical Center were taken as controls. These recordings were selected from a larger pool of ~800 EEGs to include seizures (37%), lateralized periodic discharges (1%), generalized periodic epileptiform discharges (8%), triphasic waves (3%), diffuse or focal slowing (30%), and normal (18%). Four board-certified neurologists reviewed the EEG data. Each individual's diagnosis was compared in the audio file to the ⅔ majority visual EEG diagnosis. The sensitivity of audio diagnosis was found to be as good as current gold-standard visual EEG diagnosis (table 1205). It is worth noting that the audio diagnosis is highly consistent across different individuals (even across neurologists versus non-neurologists) whereas the visual diagnosis fluctuates more depending on the level of training. While all four neurologists had more than 15 years of experience in reviewing EEGs, non-neurologists and neurologists received equal amount (only 3.5 minute) of training.

G. Computer System

Figure 13:
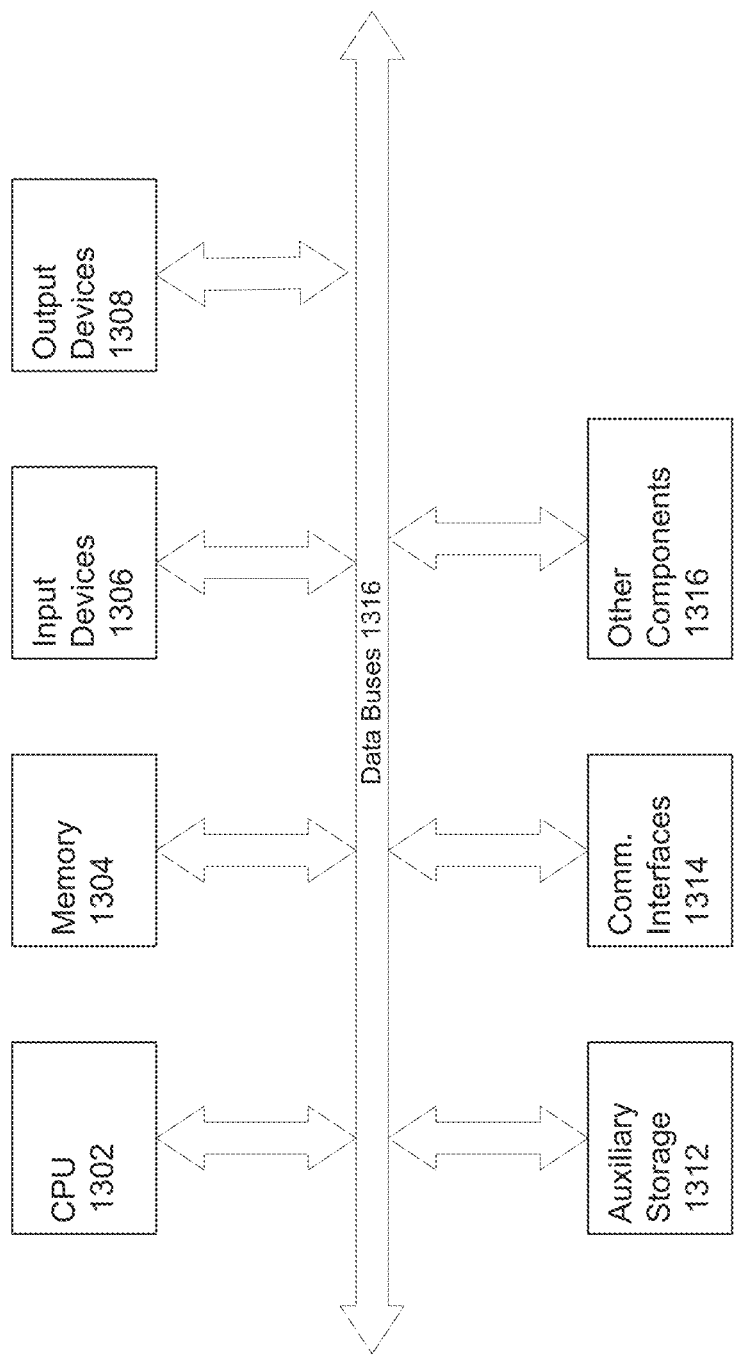
FIG. 13 is a computer system diagram in accordance with embodiments of the invention.

FIG. 13 is a computer system diagram in accordance with embodiments of the invention. Such a computer system is well-known in the art and may include the following. Computer system 1300 may include at least one central processing unit 1302 but may include many processors or processing cores. Computer system 1300 may further include memory 1304 in different forms such as RAM, ROM, hard disk, optical drives, and removable drives that may further include drive controllers and other hardware. Auxiliary storage 1312 may also be include that can be similar to memory 1304 but may be more remotely incorporated such as in a distributed computer system with distributed memory capabilities.

Computer system 1300 may further include at least one output device 1308 such as a display unit, video hardware, or other peripherals (e.g., printer). At least one input device 1306 may also be included in computer system 1300 that may include a pointing device (e.g., mouse), a text input device (e.g., keyboard), or touch screen.

Communications interfaces 1314 also form an important aspect of computer system 1300 especially where computer system 1300 is deployed as a distributed computer system. Computer interfaces 1314 may include LAN network adapters, WAN network adapters, wireless interfaces, Bluetooth interfaces, modems and other networking interfaces as currently available and as may be developed in the future.

Computer system 1300 may further include other components 1316 that may be generally available components as well as specially developed components for implementation of the present invention. Importantly, computer system 1300 incorporates various data buses 1316 that are intended to allow for communication of the various components of computer system 1300. Data buses 1316 include, for example, input/output buses and bus controllers.

Indeed, the present invention is not limited to computer system 1300 as known at the time of the invention. Instead, the present invention is intended to be deployed in future computer systems with more advanced technology that can make use of all aspects of the present invention. It is expected that computer technology will continue to advance but one of ordinary skill in the art will be able to take the present disclosure and implement the described teachings on the more advanced computers or other digital devices such as mobile telephones or "smart" televisions as they become available. Moreover, the present invention may be implemented on one or more distributed computers. Still further, the present invention may be implemented in various types of software languages including C, C++, and others. Also, one of ordinary skill in the art is familiar with compiling software source code into executable software that may be stored in various forms and in various media (e.g., magnetic, optical, solid state, etc.). One of ordinary skill in the art is familiar with the use of computers and software languages and, with an understanding of the present disclosure, will be able to implement the present teachings for use on a wide variety of computers.

H. Doctrine of Equivalents

Those skilled in the art will appreciate that the foregoing examples and descriptions of various embodiments of the present invention are merely illustrative of the invention as a whole, and that variations in the steps and various components of the present invention may be made within the spirit and scope of the invention. Accordingly, the present invention is not limited to the specific embodiments described herein but, rather, is defined by the scope of the appended claims. Moreover, where processes, workflows, and/or techniques are described as being capable of being performed in accordance with embodiments of the invention, said embodiments may be freely combined, reordered, and/or substituted with each other without departing from the spirit and scope of the invention.

Although specific sonification processes are discussed above with respect to FIG. 3 and FIG. 4 and with respect to FIGS. 8A-8C, combinations and sub-combinations of these processes can be utilized and even further specific operations of these processes can be executed in different orders without departing from the spirit of the invention. For instance, process 300 could be executed by a sonification device in accordance with a particular embodiment of the invention with portions of process 800 executed as a subprocess. Moreover, these processes can be performed by any number of sonification systems in accordance with varying embodiments of the invention. Examples of such sonification systems include (but are not limited to) the descriptions presented above with respect to FIGS. 5A and 5B and in FIGS. 5, 9, 10, and 11. Moreover, the sonification systems in accordance with multitudes of embodiments of the invention can be implemented using computing systems as described in conjunction with FIG. 13.

It will be understood that, although the terms "first," "second," etc. may be used herein to describe various elements, these elements should not be limited by these terms. These terms are only used to distinguish one element from another. For example, a first storage device could be termed a second storage device, and, similarly, a second storage device could be termed a first storage device, without changing the meaning of the description, so long as all occurrences of the "first storage device" are renamed consistently and all occurrences of the "second storage device" are renamed consistently. The first storage device and the second storage device are both storage devices, but they are not the same storage device.

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. The present disclosure provides a detailed explanation of the present invention with detailed explanations that allow one of ordinary skill in the art to implement the present invention into a computerized method. Certain of these and other details are not included in the present disclosure so as not to detract from the teachings presented herein but it is understood that one of ordinary skill in the art would be familiar with such details.

What is claimed is:

1. A device for sonifying signals, the device comprising:
    an input port configured to receive at least one electroencephalogram signal produced by a plurality of electrodes, where the at least one electroencephalogram signal is indicative of brain activity;
    an analog-to-digital converter to digitize the at least one electroencephalogram signal;
    a filter, where the filter is configured to filter non-seizure-related brain wave features from the at least one digitized signal;
    a processor that receives the at least one digitized signal and is directed by machine readable instructions to produce a sonification of the at least one electroencephalogram signal by performing a set of operations in real time comprising:
        conditioning the at least one digitized signal according to conditioning parameters, wherein conditioning said at least one digitized signal comprises boosting said signal by taking the power-law exponent of said digitized signal to enhance contrast of said signal to produce at least one conditioned signal, wherein conditioning the at least one digitized signal further comprises applying absolute value signal rectification to the digitized signal to double signal frequency and rejecting signals with an amplitude below a threshold as low-amplitude noise signals, and scaling signals above the threshold to create a fixed range boosted signal and compressing the fixed range boosted signal to raise the prominence of small features; and
        using the conditioned signal to modulate sound synthesis parameters to produce an audio signal; and
    a speaker system configured to generate sound based upon an audio signal output by the processor.

2. The device of claim 1, wherein the filter filters the at least one digitized signal utilizing filter bandpass cutoffs as part of a dual-stage filter comprising a first stage with a DC-blocking hipass filter and a second stage with a bandpass filter with a passband of 0.1-3.0 Hz to 5.0-15.0 Hz.

3. The device of claim 2, wherein at least one of DC-bias, AC line contamination, and non-seizure-related brain wave features are rejected by the dual stage filter bandpass cutoffs.

4. The device of claim 2, wherein the dual-stage filter is implemented using the processor.

5. The device of claim 1, wherein modulating the at least one digitized signal according to sound synthesis parameters further comprises continuously modulating vocal sound parameters according to sound synthesis parameters including at least one of pitch, loudness and vowel quality.

6. The device of claim 1, wherein the processor sonifies the at least one electroencephalogram signal;
    performing a formant pitch mapping on the at least one electroencephalogram signal using a midi-to-frequency function; and
    performing an inverse pitch frequency mapping on the at least one electroencephalogram signal using an interpolated look-up table for the inverse of the pitch frequency.

7. The device of claim 1 wherein compressing the fixed range boosted signal comprises compressing the fixed range signal by a factor of between 1.5 and 3.0.

8. The device of claim 1, wherein modulating the at least one boosted signal according to sound synthesis parameters to produce an audio signal comprises performing at least one process selected from the group consisting of:
    applying a pitch offset in the range of 50-150 Hz;
    performing pitch scaling to a pitch scale in the range of 110-440 Hz;
    applying an amplitude offset in the range of 0.0001-0.01;
    performing amplitude scaling in the range of 0.05-2.0;
    applying a vowel offset in the range of 0.0-1.0;
    performing vowel scaling in the range of 0.05-2.0; and
    mapping the at least one digitized signal to a vowel lookup table comprising the sounds: "iii", "ahh", "ehh", "eee", "ohh", and "ooo".

9. The device of claim 8, wherein modulating the at least one boosted signal according to sound synthesis parameters to produce an audio signal comprises:
    applying a pitch offset in the range of 50-150 Hz;
    performing pitch scaling to a pitch scale in the range of 110-440 Hz;
    applying an amplitude offset in the range of 0.0001-0.01;
    performing amplitude scaling in the range of 0.05-2.0;
    applying a vowel offset in the range of 0.0-1.0;
    performing vowel scaling in the range of 0.05-2.0; and
    mapping the at least one digitized signal to a vowel lookup table comprising the sounds: "iii", "ahh", "ehh", "eee", "ohh", and "ooo".

10. The device of claim 1, wherein the processor is directed by machine readable instructions to apply the absolute value rectification to the at least one digitized signal prior to taking the power-law exponent.

11. A method for sonifying signals using a sonification device, the method comprising:
    receiving at least one electroencephalogram signal produced by a plurality of electrodes using an input port of a sonification device, where the at least one electroencephalogram signal is indicative of brain activity;

digitizing the at least one electroencephalogram signal using an analog-to-digital converter of the sonification device;

filtering non-seizure-related brain wave features from the at least one digitized signal using a filter of the sonification device;

producing a sonification of the at least one encephalogram signal by performing a set of operations in real time using a processor of the sonification device, the set of operations comprising:

conditioning the at least one digitized signal according to conditioning parameters, wherein conditioning said at least one digitized signal comprises (a) boosting said signal by taking the power-law exponent of said digitized signal to enhance contrast of said signal to produce at least one conditioned signal, wherein conditioning the at least one digitized signal further comprises applying absolute value signal rectification to the digitized signal to double signal frequency, (b) rejecting signals with an amplitude below a threshold as low-amplitude noise signals, (c) scaling signals above the threshold to create a fixed range boosted signal, and (d) compressing the fixed range boosted signal to raise the prominence of small features; and using the conditioned signal to modulate sound synthesis parameters to produce an audio signal; and generating sound based upon the audio signal using a speaker system of the sonification device.

12. The method of claim 11, wherein the filter of the sonification device filters the at least one digitized signal utilizing filter bandpass cutoffs as part of a dual-stage filter comprising a first stage with a DC-blocking hipass filter and a second stage with a bandpass filter with a passband of 0.1-3.0 Hz to 5.0-15.0 Hz.

13. The method of claim 12, wherein at least one of DC-bias, AC line contamination, and non-seizure related brain wave features are rejected by dual stage filtering.

14. The method of claim 11, wherein modulating the at least one digitized signal according to sound synthesis parameters further comprises continuously modulating vocal sound parameters according to sound synthesis parameters including at least one of pitch, loudness and vowel quality.

15. The method of claim 11, wherein the processor sonifies the at least one electroencephalogram signal by:

performing a formant pitch mapping on the at least one electroencephalogram signal using a midi-to-frequency function; and performing an inverse pitch frequency mapping on the at least one electroencephalogram signal using an interpolated look-up table for the inverse of the pitch frequency.

16. The method of claim 11, wherein filtering is implemented using the processor.

17. The device of claim 11, wherein compressing the fixed range signal comprises compressing the fixed range boosted signal by a factor of between 1.5 and 3.0.

18. The method of claim 11, wherein modulating the at least one boosted signal according to sound synthesis parameters to produce an audio signal comprises performing at least one process selected from the group consisting of:

applying a pitch offset in the range of 50-150 Hz;
performing pitch scaling to a pitch scale in the range of 110-440 Hz;
applying an amplitude offset in the range of 0.0001-0.01;
performing amplitude scaling in the range of 0.05-2.0;
applying a vowel offset in the range of 0.0-1.0;
performing vowel scaling in the range of 0.05-2.0; and
mapping the at least one digitized signal to a vowel lookup table comprising the sounds: "iii", "ahh", "ehh", "eee", "ohh", and "ooo".

19. The method of claim 18, wherein modulating the at least one boosted signal according to sound synthesis parameters to produce an audio signal comprises:

applying a pitch offset in the range of 50-150 Hz;
performing pitch scaling to a pitch scale in the range of 110-440 Hz;
applying an amplitude offset in the range of 0.0001-0.01;
performing amplitude scaling in the range of 0.05-2.0;
applying a vowel offset in the range of 0.0-1.0;
performing vowel scaling in the range of 0.05-2.0; and
mapping the at least one digitized signal to a vowel lookup table comprising the sounds: "iii", "ahh", "ehh", "eee", "ohh", and "ooo".

20. The method of claim 11, further comprising:

detecting occurrence of a seizure by ear based upon sound generated from the speaker system of the sonification device; and administering treatment in response to the detection of a seizure to interrupt the seizure.

21. The method of claim 11, wherein absolute value rectification is applied to the at least one digitized signal prior to taking the power-law exponent.

* * * * *